(12) United States Patent
Lazzari et al.

(10) Patent No.: US 6,221,937 B1
(45) Date of Patent: *Apr. 24, 2001

(54) TRIAZINE COMPOUNDS CONTAINING 2,2,6, 6-TETRAMETHYL-4-PIPERIDYL GROUPS AS STABILIZERS FOR ORGANIC MATERIALS

(75) Inventors: Dario Lazzari; Fabrizio Guizzardi, both of Bologna (IT)

(73) Assignee: Ciba Specialty Chemicals Corporation, Tarrytown, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/426,025

(22) Filed: Oct. 25, 1999

Related U.S. Application Data

(63) Continuation of application No. 08/994,977, filed on Dec. 19, 1997, now abandoned.

(30) Foreign Application Priority Data

Dec. 24, 1996 (EP) .................................. 96810902
Feb. 12, 1997 (EP) .................................. 97810075

(51) Int. Cl.⁷ ....................................... C08J 7/08
(52) U.S. Cl. .......................................... 524/100
(58) Field of Search ........................................... 524/100

(56) References Cited

U.S. PATENT DOCUMENTS

| | | | |
|---|---|---|---|
| 3,898,303 | 8/1975 | Murayama et al. | 260/880 |
| 4,086,204 | 4/1978 | Cassandrini et al. | 260/45.8 |
| 4,108,829 | 8/1978 | Cassandrini et al. | 260/45.8 |

(List continued on next page.)

FOREIGN PATENT DOCUMENTS

| | | |
|---|---|---|
| 19541332 | 11/1995 | (DE) . |
| 0074598 | 3/1983 | (EP) . |
| 0094048 | 11/1983 | (EP) . |
| 0357223 | 3/1990 | (EP) . |
| 0377324 | 7/1990 | (EP) . |
| 0627428 | 12/1994 | (EP) . |
| 0782994 | 7/1997 | (EP) . |
| 9521157 | 8/1995 | (WO) . |

OTHER PUBLICATIONS

O.A. Battista: Fundamentals of High Polymers—pp. 73–74, 1958.*
Patent Abstracts of Japan, vol. 10, No. 390, Dec. 1986, JP 61176662.
Derwent Abstr. 86–248801/38.

Primary Examiner—Veronica P. Hoke
(74) Attorney, Agent, or Firm—Tyler A. Stevenson

(57) ABSTRACT

A product of the formula (I)

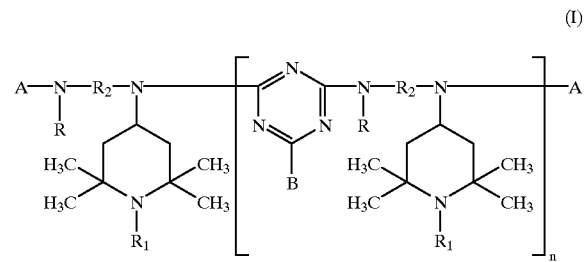

(I)

in which n is a number from 2 to 14; the radicals $R_1$ are for example hydrogen or $C_1$–$C_8$alkyl; $R_2$ is for example $C_2$–$C_{12}$alkylene; the radicals A are for example $C_1$–$C_8$acyl; the radicals B are independently of one another —$OR_3$, —$N(R_4)(R_5)$ or a group of the formula

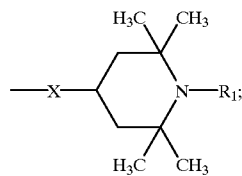

$R_3$, $R_4$ and $R_5$, which are identical or different, are for example hydrogen or $C_1$–$C_{18}$alkyl, or —$N(R_4)(R_5)$ is additionally a group of the formula

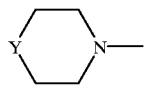

with Y being —O—, —$CH_2$—, —$CH_2CH_2$— or >N—$CH_3$; X is —O— or >N—$R_6$; $R_6$ is for example hydrogen or $C_1$–$C_{18}$alkyl; R is preferably a group of the formula

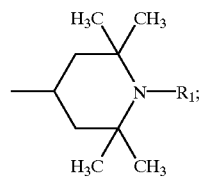

with the proviso that in the individual recurrent units of the formula (I), each of the radicals B, R, $R_1$ and $R_2$ has the same or a different meaning.

The indicated product is useful as light stabilizer, heat stabilizer and oxidation stabilizer for organic materials, in particular synthetic polymers.

27 Claims, 8 Drawing Sheets

U.S. PATENT DOCUMENTS

| | | | |
|---|---|---|---|
| 4,234,707 | 11/1980 | Rody et al. | 525/437 |
| 4,315,859 | 2/1982 | Nikles | 544/198 |
| 4,316,837 | 2/1982 | Molt et al. | 260/45.8 |
| 4,331,586 | 5/1982 | Hardy | 525/186 |
| 4,335,242 | 6/1982 | Wiezer et al. | 544/198 |
| 4,415,689 | 11/1983 | Minagawa et al. | 524/103 |
| 4,442,250 | 4/1984 | Cantatore | 524/98 |
| 4,459,395 | 7/1984 | Cantatore | 524/100 |
| 4,468,488 | 8/1984 | Minagawa et al. | 524/99 |
| 4,492,791 | 1/1985 | Orban et al. | 544/198 |
| 4,743,688 | 5/1988 | Minagawa et al. | 544/113 |
| 5,047,531 | 9/1991 | Cantatore et al. | 544/198 |
| 5,130,429 | 7/1992 | Piccinelli et al. | 544/212 |
| 5,198,546 | 3/1993 | Borzatta et al. | 544/198 |
| 5,324,834 | 6/1994 | Borzatta et al. | 544/198 |
| 5,449,776 | 9/1995 | Vignali et al. | 544/198 |
| 5,610,211 | 3/1997 | Borzatta et al. | 524/100 |
| 5,847,132 | 12/1998 | Borzatta et al. | 544/198 |

\* cited by examiner

EXAMPLE 6-B
$\overline{Mw}/\overline{Mn}=1.35$

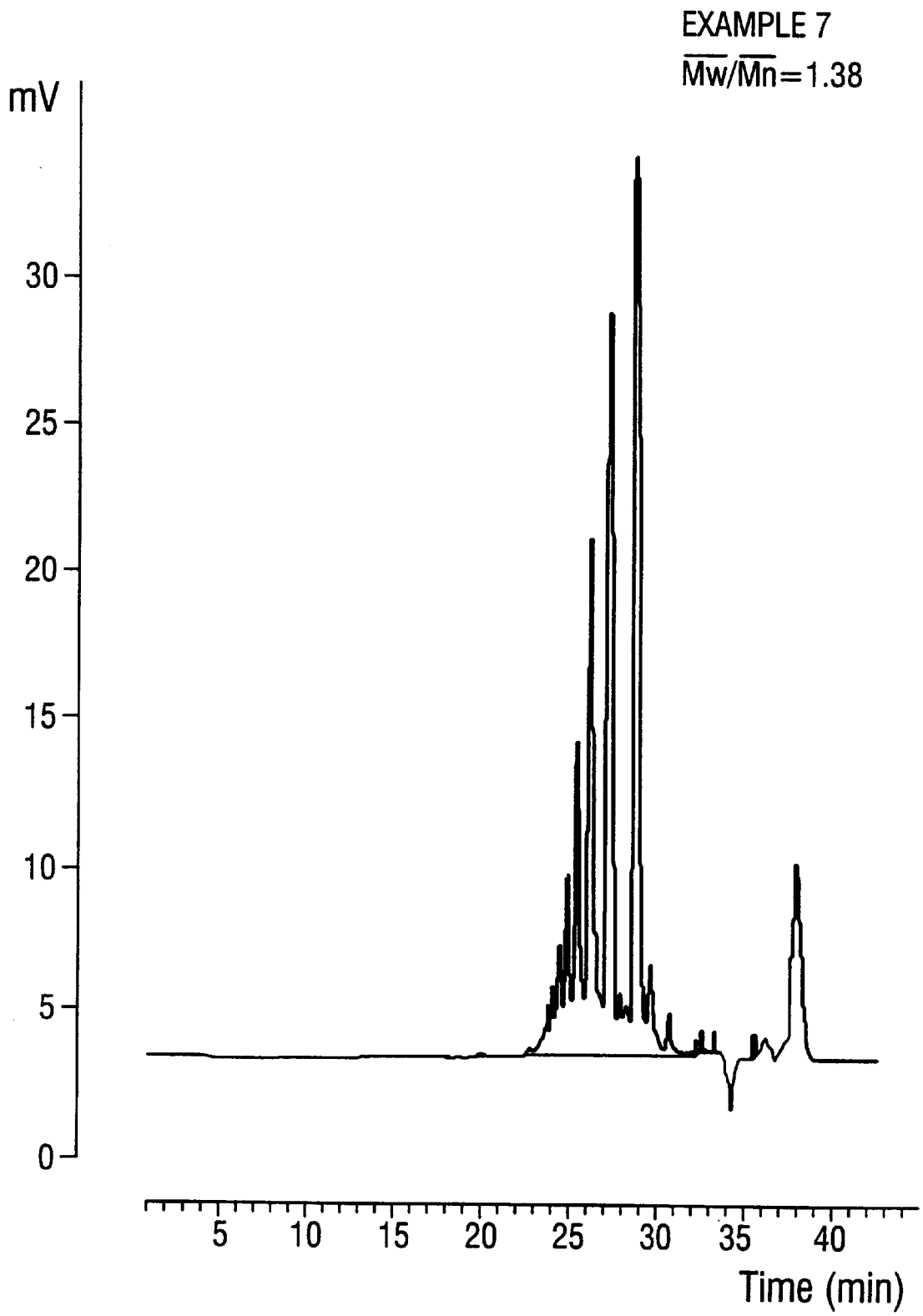

TRIAZINE COMPOUNDS CONTAINING 2,2,6,6-TETRAMETHYL-4-PIPERIDYL GROUPS AS STABILIZERS FOR ORGANIC MATERIALS

This is a continuation of application Ser. No. 08/994,977, filed Dec. 19, 1997, abandoned.

The present invention relates to triazine compounds containing 2,2,6,6-tetramethyl-4-piperidyl groups, to their use as light stabilizers, heat stabilizers and oxidation stabilizers for organic materials, particularly synthetic polymers, and to the organic materials thus stabilized. Furthermore, the present invention relates to specific block oligomers as well as to a mixture of block oligomers with a narrow molecular weight distribution, and to a method of the preparation thereof.

The stabilization of synthetic polymers with derivatives of 2,2,6,6-tetramethylpiperidine has been described for example in U.S. Pat. No. 4,086,204, U.S. Pat. No. 4,331,586, U.S. Pat. No. 4,335,242, U.S. Pat. No. 4,234,707, U.S. Pat. No. 5,198,546, U.S. Pat. No. 5,610,211, U.S. Pat. No. 5,449,776, U.S. Pat. No. 5,047,531, U.S. Pat. No. 4,468,488, U.S. Pat. No. 4,415,689, EP-A-357 223, EP-A-377 324 and Derwent 86-248801/38.

The present invention relates in particular to a product of the formula (I)

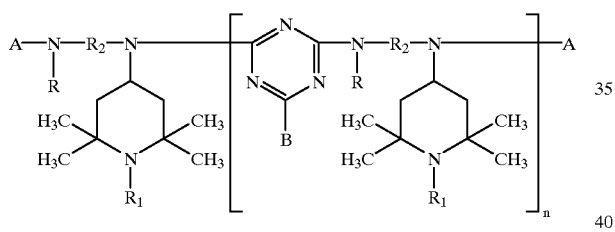

(I)

in which n is a number from 2 to 14;

the radicals $R_1$ are independently of one another hydrogen, $C_1$–$C_8$alkyl, $C_1$–$C_8$hydroxyalkyl, —$CH_2CN$, $C_3$–$C_6$alkenyl, $C_3$–$C_6$alkynyl, $C_7$–$C_9$phenylalkyl which is unsubstituted or substituted on the phenyl by 1, 2 or 3 $C_1$–$C_4$alkyl; $C_1$–$C_8$acyl, ($C_1$–$C_8$alkoxy)carbonyl or ($C_5$–$C_{12}$cycloalkoxy)carbonyl;

$R_2$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N-$X_1$ with $X_1$ being $C_1$–$C_{12}$acyl or ($C_1$–$C_{12}$alkoxy)carbonyl or having one of the definitions of $R_4$ given below except hydrogen; or $R_2$ is a group of the formula (a), (b) or (c);

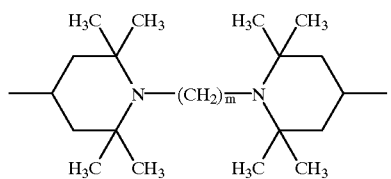

(a)

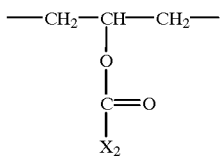

(b)

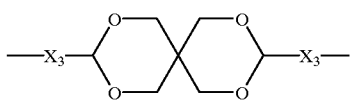

(c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another $C_1$–$C_8$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$;

B is $OR_3$, —$N(R_4)(R_5)$ or a group of the formula (II);

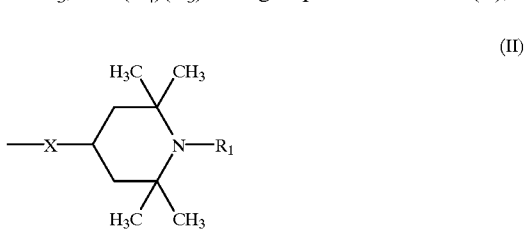

(II)

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted, or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

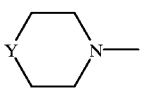

(III)

with Y being —O—, —$CH_2$—, —$CH_2CH_2$— or >N—$CH_3$, or —$N(R_4)(R_5)$ is additionally a group of the formula (III);

X is —O— or >N-$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

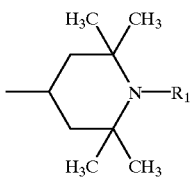

or $C_2$–$C_4$alkyl which is substituted in the 2, 3 or 4 position by —OH, $C_1$–$C_8$alkoxy, di($C_1$–$C_4$alkyl)amino or a group of the formula (III); and R has one of the meanings given for $R_6$;

with the proviso that in the individual recurrent units of the formula (I), each of the radicals B, R, $R_1$ and $R_2$ has the same or a different meaning.

In the individual recurring units of the formula (I), each of the radicals B, R, $R_1$ and $R_2$ has preferably the same meaning.

In the formula (I), the radical R and the radical

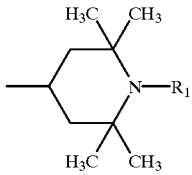

can have a random distribution or a block distribution.

R is preferably different from hydrogen, when A is $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$, in particular $C_1$–$C_8$alkyl.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. One of the preferred meanings of A is $C_1$–$C_4$alkyl.

An example of $C_2$–$C_8$hydroxyalkyl and of $C_2$–$C_4$alkyl substituted by —OH is 2-hydroxyethyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (III) is preferably

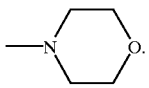

Preferred examples of $C_2$–$C_4$alkyl substituted by a group of the formula (III) are groups of the formula

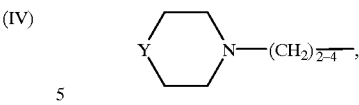

The group

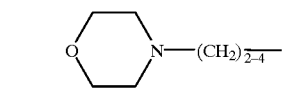

is particularly preferred.

Examples of alkoxy containing not more than 8 carbon atoms are methoxy, ethoxy, propoxy, isopropoxy, butoxy, isobutoxy, pentoxy, isopentoxy, hexoxy, heptoxy or octoxy.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclodecyl. Unsubstituted or substituted cyclohexyl is preferred.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred, and allyl is particularly preferred.

An example of $C_3$–$C_6$alkynyl is 2-butynyl.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl by 1, 2 or 3 $C_1$–$C_4$alkyl are benzyl, methylbenzyl, dimethylbenzyl, trimethylbenzyl, t-butylbenzyl and 2-phenylethyl. Benzyl is preferred.

Examples of acyl (aliphatic, cycloaliphatic or aromatic) containing not more than 12 carbon atoms are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred. One of the preferred meanings of A is $C_1$–$C_2$acyl, in particular formyl or acetyl.

Examples of alkoxycarbonyl with the alkoxy group having up to 12 carbon atoms are methoxycarbonyl, ethoxycarbonyl, propoxycarbonyl, butoxycarbonyl, pentoxycarbonyl, hexoxycarbonyl, heptoxycarbonyl, octoxycarbonyl, nonyloxycarbonyl, decyloxycarbonyl, undecyloxycarbonyl and dodecyloxycarbonyl. One of the preferred meanings of A is ($C_1$–$C_2$alkoxy)carbonyl.

A particularly preferred example of ($C_5$–$C_{12}$cycloalkoxy) carbonyl is cyclohexoxycarbonyl. ($C_5$–$C_7$cycloalkoxy) carbonyl is preferred.

Examples of ($C_1$–$C_8$alkyl)aminocarbonyl are methylaminocarbonyl, ethylaminocarbonyl, propylaminocarbonyl, butylaminocarbonyl, pentylaminocarbonyl, hexylaminocarbonyl, heptylaminocarbonyl and octylaminocarbonyl. ($C_1$–$C_4$alkyl) aminocarbonyl is preferred.

A particularly preferred example of ($C_5$–$C_{12}$cycloalkyl) aminocarbonyl is cyclohexylaminocarbonyl. ($C_5$–$C_7$cycloalkyl)aminocarbonyl is preferred.

A particularly preferred example of ($C_7$–$C_9$phenylalkyl) aminocarbonyl is benzylaminocarbonyl.

Examples of alkylene containing not more than 12 carbon atoms are ethylene, propylene, trimethylene, tetramethylene, pentamethylene, hexamethylene, octamethylene, decamethylene and dodecamethylene. $R_2$ is for example $C_2$–$C_8$alkylene or $C_4$–$C_8$alkylene, in particular $C_2$–$C_6$alkylene, preferably hexamethylene.

An example of $C_4$–$C_{12}$alkenylene is 3-hexenylene.

An example of $C_5$–$C_7$cycloalkylene is cyclohexylene.

Examples of $C_4$–$C_{12}$alkylene interrupted by 1,4-piperazinediyl are

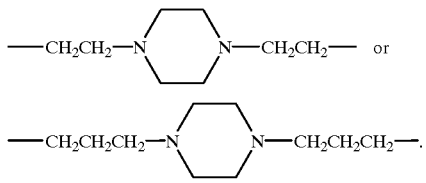

Examples of $C_4$–$C_{12}$alkylene interrupted by —O—, e.g. 1, 2 or 3 —O—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Examples of $C_4$–$C_{12}$alkylene interrupted by >N-$X_1$ are —CH$_2$CH$_2$CH$_2$-N($X_1$)—CH$_2$CH$_2$-N($X_1$)—CH$_2$CH$_2$CH$_2$—, in particular —CH$_2$CH$_2$CH$_2$N(CH$_3$)—CH$_2$CH$_2$-N(CH3)—CH$_2$CH$_2$CH$_2$—.

An example of $C_5$–$C_7$cycloalkylenedi($C_1$–$C_4$alkylene) is cyclohexylenedimethylene.

Examples of $C_1$–$C_4$alkylenedi($C_5$–$C_7$cycloalkylene) are methylenedicyclohexylene and isopropylidenedicyclohexylene.

An example of phenylenedi($C_1$–$C_4$alkylene) is phenylenedimethylene.

R is preferably hydrogen, $C_1$–$C_{10}$alkyl, cyclohexyl or a group of the formula (IV), in particular a group of the formula (IV).

The radicals $R_1$ are preferably independently of one another hydrogen, $C_1$–$C_4$alkyl, allyl, benzyl or acetyl. Hydrogen and methyl are particularly preferred.

A is preferably acetyl, ($C_1$–$C_2$alkoxy)carbonyl, ($C_1$–$C_2$alkyl)aminocarbonyl or $C_1$–$C_4$alkyl.

The radical B is preferably a group —NH($C_1$–$C_8$alkyl) or —N($C_1$–$C_8$alkyl)$_2$ or a group

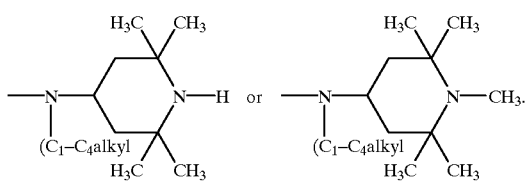

The variable n is preferably a number from 2 to 8, in particular 2 to 6.

A preferred embodiment of the present invention is a compound of the formula (I) with a polydispersity $\overline{Mw}/\overline{Mn}$ of 1 and n being 2, 3, 4, 5, 6, 7, 8, 9, 10, 11, 12, 13 or 14. The compound can be named as "block oligomer". This embodiment is of interest, when A is $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —CH$_2$CN, in particular $C_1$–$C_8$alkyl, for example methyl.

Polydispersity indicates the molecular-weight distribution of a polymeric compound. In the present application, the polydispersity is the ratio of weight-average ($\overline{Mw}$) and number-average ($\overline{Mn}$) molecular weights. A value of $\overline{Mw}/\overline{Mn}$ equal to 1 means that the compound is monodispers and has only one molecular weight and no molecular weight distribution.

A preferred embodiment of the present invention relates to a product of the formula (I) wherein $R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene); the radicals A are independently of one another $C_1$–$C_8$acyl, ($C_1$–$C_8$alkoxy)carbonyl, ($C_5$–$C_7$cycloalkoxy)carbonyl, ($C_1$–$C_4$alkyl)aminocarbonyl, ($C_5$–$C_7$cycloalkyl)aminocarbonyl, benzylaminocarbonyl, $C_1$–$C_6$alkyl, $C_5$–$C_7$cycloalkyl, allyl or benzyl; $R_3$, $R_4$ and $R_5$, which are identical or different, are hydrogen, $C_1$–$C_{12}$alkyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (III); or —N($R_4$)($R_5$) is additionally a group of the formula (III); and $R_6$ is hydrogen, $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; tetrahydrofurfuryl, a group of the formula (IV) or $C_2$–$C_3$alkyl which is substituted in the 2 or 3 position by —OH, $C_1$–$C_4$alkoxy, di($C_1$–$C_4$alkyl)amino or a group of the formula (Ill).

A preferred product of the formula (I) is that wherein $R_2$ is $C_2$–$C_8$alkylene;

the radicals A are independently of one another $C_1$–$C_8$acyl, ($C_1$–$C_8$alkoxy)carbonyl, cyclohexoxycarbonyl, ($C_1$–$C_4$alkyl)aminocarbonyl, cyclohexylaminocarbonyl, benzylaminocarbonyl, $C_1$–$C_4$alkyl, cyclohexyl, allyl or benzyl;

$R_3$, $R_4$ and $R_5$, which are identical or different, are hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —N($R_4$)($R_5$) is additionally 4-morpholinyl; and $R_6$ is hydrogen, $C_1$–$C_8$alkyl, cyclohexyl which is unsubstituted or substituted by methyl; benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

A particularly preferred product of the formula (I) is that wherein n is a number from 2 to 6, preferably 2, 4 or 6;

the radicals $R_1$ are independently of one another hydrogen or methyl;

$R_2$ is $C_2$–$C_6$alkylene;

the radicals A are independently of one another $C_1$–$C_8$acyl, ($C_1$–$C_8$alkoxy)carbonyl, ($C_1$–$C_4$alkyl)aminocarbonyl, $C_1$–$C_4$alkyl or allyl;

the radicals B are independently of one another —N($R_4$)($R_5$) or a group of the formula (II);

$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl;

X is >N$R_6$; and $R_6$ is $C_1$–$C_4$alkyl.

BRIEF DESCRIPTION OF DRAWINGS

A further embodiment of the present invention is a mixture containing at least three different monodispers compounds of the formula (I) which vary only by the variable n, said mixture having a polydispersity $\overline{Mw}/\overline{Mn}$ of 1.1 to 1.7, for example 1.1 to 1.65, 1.1 to 1.6, 1.1 to 1.55 or 1.1 to 1.5, preferably 1.1 to 1.45. This embodiment is of special interest, when A is $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$, in particular $C_1$–$C_8$alkyl, for example methyl.

FIGS. 1–8 are chromatograms of various mixtures obtained by GPC (Gel Permeation Chromatography) from which measurements the products' polydispersity ratings were determined.

Figure 1:
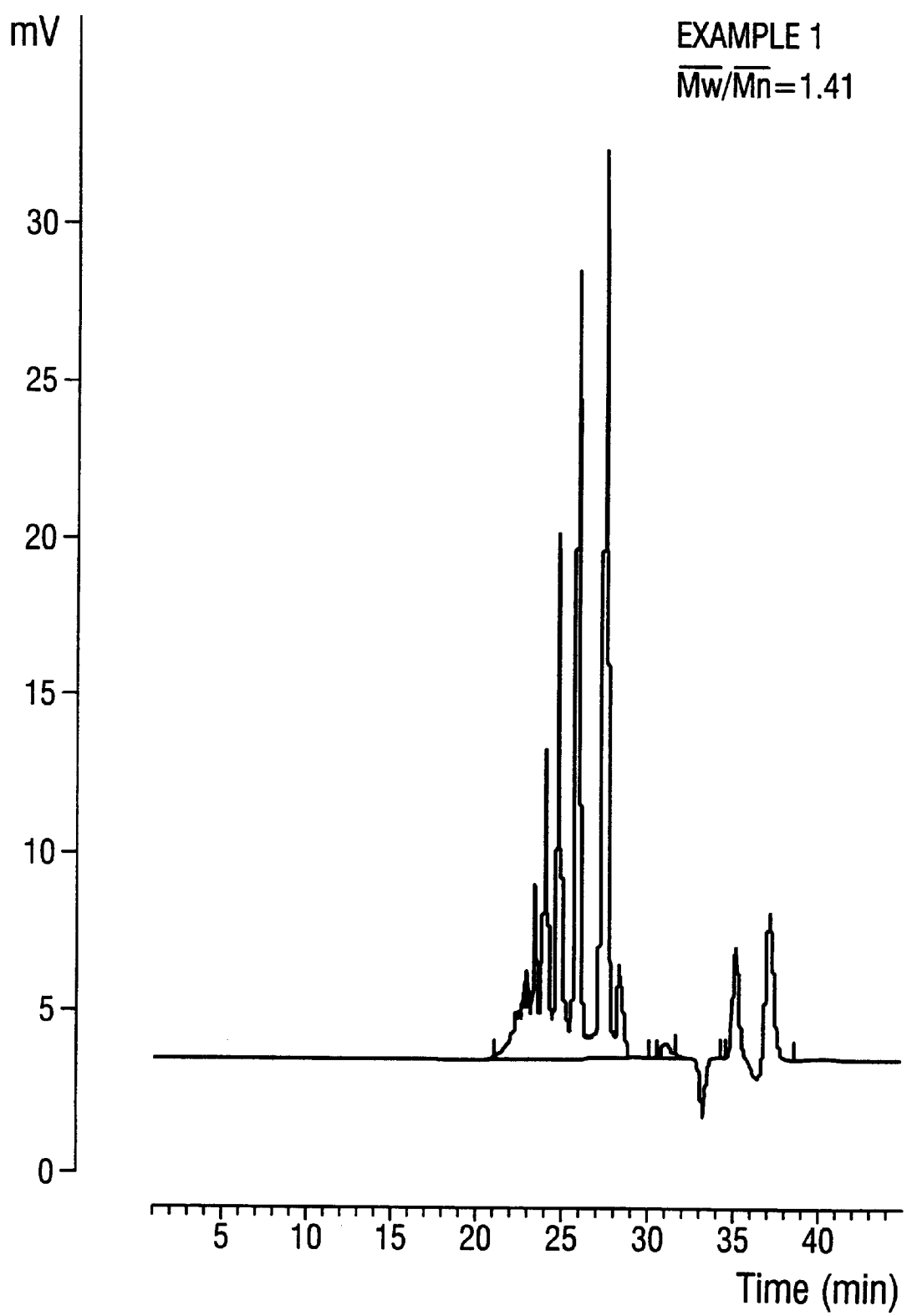

Further examples for the polydispersity $\overline{Mw}/\overline{Mn}$ are 1.2 to 1.7, for example 1.2 to 1.65, 1.2 to 1.6, 1.2 to 1.55 or 1.2 to 1.5, preferably 1.2 to 1.45.

A preferred mixture contains a) a monodispers compound of the formula (Ia),

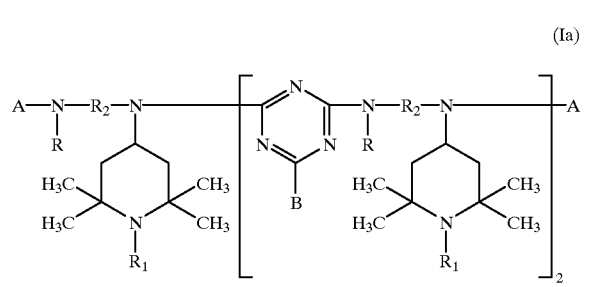

(Ia)

b) a monodispers compound of the formula (Ib) and

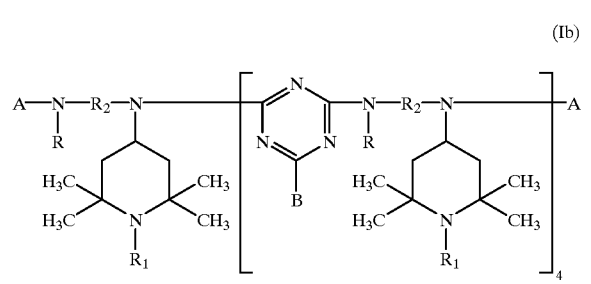

(Ib)

c) a monodispers compound of the formula (Ic)

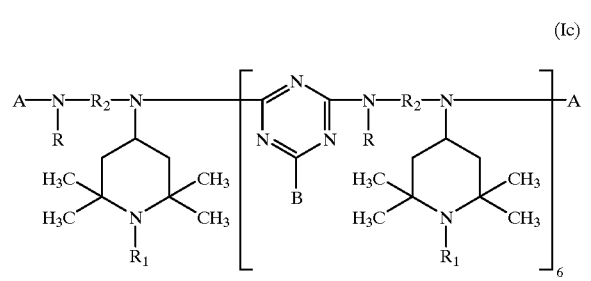

(Ic)

wherein A, B, R, $R_1$ and $R_2$ are in the formulae (Ia), (Ib) and (Ic) identical and are as defined above, and the molar ratio of the compounds of the formula (Ia) to (Ib) to (Ic) is 2:2:1.5 to 2:0.5:0.05, in particular 2:1.5:1 to 2:0.5:0.08 or 2:1:0.5 to 2:0.5:0.08.

The described mixtures can additionally contain a compound of the formula (Id) and/or (Ie),

(Id)

(Ie)

These compounds may be present in the mixtures in an amount of 30% to 0.5%, preferably 20% to 0.5% or 8% to 0.5% with regard to the weight of the total mixture.

The preferred embodiments indicated above for the products of the formula (I) also relate to the monodispers compounds and the mixtures thereof with the indicated polydispersity.

A particularly preferred mixture is one containing a monodispers compound of the formula (Ia), a monodispers compound of the formula (Ib) and a monodispers compound of the formula (Ic) wherein the radicals $R_1$ are independently of one another hydrogen or methyl;

$R_2$ is $C_2$–$C_6$alkylene;

A is acetyl, ($C_1$–$C_2$alkoxy)carbonyl, (C–$C_2$alkyl)aminocarbonyl or $C_1$–$C_4$alkyl;

B is —$N(R_4)(R_5)$ or a group of the formula (II) with $R_1$ being as defined above;

$R_4$ and $R_5$, which are identical or different, are hydrogen, $C_1$–$C_8$alkyl, 2-hydroxyethyl or 2-methoxyethyl or —$N(R_4)(R_5)$ is additionally 4-morpholinyl;

X is >$NR_6$;

$R_6$ is $C_1$–$C_4$alkyl; and

R is a group of the formula (IV) with $R_1$ being as defined above.

A further embodiment of the present invention is a method for preparing a mixture having the polydispersity indicated above and containing at least three different monodispers compounds of the formula (I), which comprises 1) reacting a compound of the formula (A)

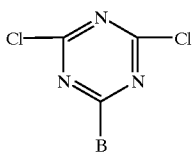
(A)

with a compound of the formula (B)

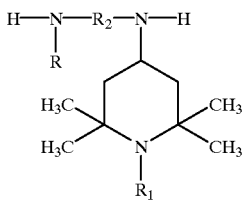
(B)

in a stoichiometric ratio to obtain a compound of the formula (C);

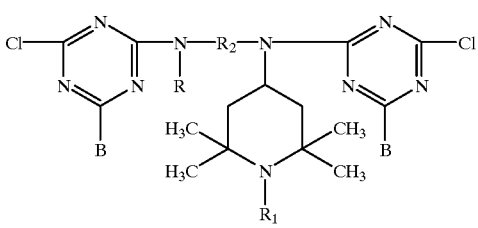
(C)

2) reacting a compound of the formula (C) with a compound of the formula (B) in a molar ratio of 1:2 to 1:3, preferably 1:2 to 1:2.5, in particular in a molar ratio of 1:2, to obtain a mixture of at least three different monodispers compounds of the formula (D) with n being 2, 3, 4, 5, 6, 7, 8, 9, 10, 11, 12, 13 or 14 or being 2, 3, 4, 5, 6, 7, 8, 9, 10, 11 or 12, preferably 2, 3, 4, 5, 6, 7, 8, 9 or 10, or preferably 2, 3, 4, 5, 6, 7 or 8, in particular 2, 4 and 6;

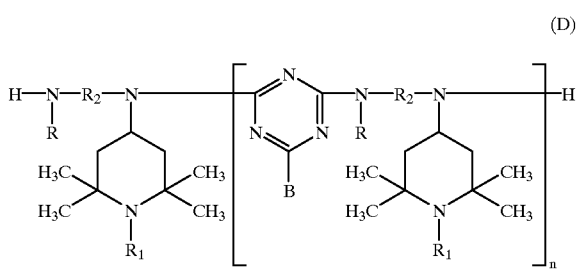
(D)

3) reacting the mixture obtained in 2) with a compound of the formula (E) or with a compound of the formula (F)

A'—X'  (E)

A"—NCO  (F)

wherein X' is a leaving group, for example halogen, in particular chlorine;

A' is $C_1$–$C_8$acyl, ($C_1$–$C_8$alkoxy)carbonyl, ($C_5$–$C_{12}$cycloalkoxy)carbonyl, $C_1$–$C_8$alkyl, $C_5$–$C_{12}$cycloalkyl which is unsubstituted or substituted by 1, 2 or 3 $C_1$–$C_4$alkyl, $C_{-}C_6$alkenyl, $C_7$–$C_9$phenylalkyl which is unsubstituted or substituted on the phenyl by 1, 2 or 3 $C_1$–$C_4$alkyl; or —$CH_2CN$; and A" is $C_1$–$C_8$alkyl, $C_5$–$C_{12}$cycloalkyl or $C_7C_9$phenylalkyl;

in about a stoichiometric ratio to obtain the desired mixture;

the reactions 1) to 3) being carried out in an organic solvent in the presence of an inorganic base with the proviso that, when in the reaction 3) a compound of the formula (F) is applied, said reaction 3) is carried out without any inorganic base.

When A is $C_1$–$C_8$acyl, the reaction 3) may also be carried out with the corresponding acid anhydride as reagent instead of a compound of the formula (E).

When A is a methyl group, the product of the formula (I) can also be obtained by reacting a mixture of formaldehyde/formic acid with a compound of the formula (D) as described for example in U.S. Pat. No. 5,130,429 or in U.S. Pat. No. 3,898,303.

Examples for suitable organic solvents are toluene, xylene, trimethylbenzene, isopropylbenzene, diisopropylbenzene and essentially water-insoluble organic ketones such as, for example, methyl isobutyl ketone. Xylene is preferred.

Examples for an inorganic base are sodium hydroxide, potassium hydroxide, sodium carbonate and potassium carbonate. Sodium hydroxide is preferred.

The reaction 1) is carded out, for example, at a temperature of 40° C. to 70° C., preferably 50° C. to 60° C.

The reaction 2) is carried out, for example, at a temperature of 110° C. to 180° C., preferably 140° C. to 160° C.

When the reactant of the formula (E) is used in the reaction 3), said reaction 3) is carried out, for example, at a temperature of 60° C. to 180° C., preferably of 146° C. to 160° C., if necessary in a closed vessel.

When the reactant of the formula (F) is used in the reaction 3), said reaction 3) is carried out, for example, at a temperature of 0° C. to 60° C., preferably of 0° C. to 25° C.

Possible by-products are the above shown compounds of the formula (Id) and/or (Ie).

The compound of the formula (A) can be prepared, for example, by reacting cyanuric chloride with a compound B-H in a stoichiometric ratio in the presence of an organic solvent and an inorganic base.

It is appropriate to use for the preparation of the compounds of the formula (A) the same solvent and the same inorganic base than in the above indicated reactions 1) to 3).

The starting materials used in the above process are known. In the case that they are not commercially available, they can be prepared analogously to known methods. For example, some starting materials of the formula (B) are described in WO-A-95/21157, U.S. Pat. No. 4,316,837 and U.S. Pat. No. 4,743,688.

An embodiment of the present invention is also a mixture obtainable by the above indicated process.

A compound of the formula (I) with a polydispersity / of 1 may be prepared by building up said compound step by step. A representative example for such a procedure is as follows:

The intermediate of the formula (D) with n being 2 corresponds to the formula

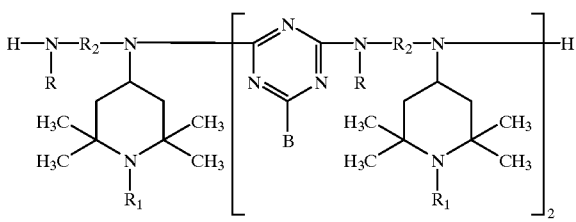

and can be prepared by reacting a compound of the formula (C) with a compound of the formula (B) in a molar ratio of 1:10 to 1:50, preferably 1:20 to 1:40, in particular 1:20 to 1:35. The reaction may be carried out e.g. in an organic solvent or neat in the presence of an inorganic base. The solvent and/or the excess of the reactant of the formula (B) can be eliminated by distillation at the appropriate conditions. Examples for an organic solvent are toluene, xylene, trimethylbenzene, isopropylbenzene and diisopropylbenzene. Xylene is preferred. Examples for an inorganic base are sodium hydroxide, potassium hydroxide, sodium carbonate and potassium carbonate. Sodium hydroxide is preferred. The reaction is carried out at a temperature of, for example, 110° C. to 180° C., preferably 140° C. to 160° C.

Subsequently, the intermediate obtained is conveniently reacted with an acylating or alkylating agent according to the conditions of the above described reaction 3).

A product of the formula (I) which is not characterized by a particular polydispersity can be prepared, for example, by reacting a compound of the formula (A) with an excess of up to 10% by mole of a compound of the formula (B) without controlling the building up of the molecule. Subsequently, the product obtained may be reacted with a compound of the formula (E) or (F) as described above.

The product of the formula (I) as well as the monodispers compound of the formula (I) and the described mixtures with a narrow molecular weight distribution are very effective in improving the light, heat and oxidation resistance of organic materials, especially synthetic polymers and copolymers. In particular, a low pigment interaction as well as a very good color in the presence of phenolic antioxidants are observed in polypropylene, especially polypropylene fibres. Therefore, the product of the formula (I) is particularly useful for stabilizing pigmented polyolefins, preferably polypropylene. Furthermore, a very good resistance of the polypropylene to gas fading is observed.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLOPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(a-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or poly tetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenolF, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention thus also relates to a composition comprising an organic material susceptible to degradation induced by light, heat or oxidation and a product of the formula (I).

The totality of the compounds of the formula (I) being present in the composition has preferably a polydispersity $\overline{M}w/\overline{M}n$ of 1 to 1.7, for example 1 to 1.65, 1 to 1.6, 1 to 1.55, 1 to 1.5 or 1 to 1.45.

The invention further relates to a composition comprising an organic material susceptible to degradation induced by light, heat or oxidation and a mixture containing at least three different monodispers compounds of the formula (I) which vary only by the variable n, said mixture having a polydispersity $\overline{M}w/\overline{M}n$ of 1.1 to 1.7 or 1.1 to 1.5, with the proviso that the totality of the compounds of the formula (I) being present in the composition has a polydispersity $\overline{M}w/\overline{M}n$ of 1.1 to 1.7 or 1.1 to 1.5.

The organic material is preferably a synthetic polymer, more particularly one selected from the aforementioned groups. Polyolefins are preferred and polyethylene and polypropylene are particularly preferred.

A further embodiment of the present invention is a method for stabilizing an organic material against degradation induced by light, heat or oxidation, which comprises incorporating into said organic material a product of the formula (I).

The product of the formula (I) can be used in various proportions depending on the nature of the material to be stabilized, on the end use and on the presence of other additives.

In general, it is appropriate to use, for example, 0.01 to 5% by weight of the product of the formula (I), relative to the weight of the material to be stabilized, preferably 0.05 to 1%.

The product of the formula (I) can be added, for example, to the polymeric materials before, during or after the polymerization or crosslinking of the said materials. Furthermore, it can be incorporated in the polymeric materials in the pure form or encapsulated in waxes, oils or polymers.

In general, the product of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the product of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the product of the formula (I).

Particular examples of said conventional additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-di-methylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-di-methyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino) 1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3.5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)-oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3.5-di-tert-butyl-4-hydroxyphenylpropionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N N,N',N'-tetramethyl-4,4'-diaminodiphenylmethane, 1,2-bis[(2-methylphenyl)amino]ethane, 1,2-bis(phenylamino)propane, (o-tolyl)biguanide, Bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotrazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyl oxy)carbonylethyl]-2'-hydroxyphenyl)benzotriazole, 2-(3'- dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol300; [R—CH$_2$CH$_2$—COO(CH$_2$)$_3$-]$_2$ where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyl-oxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxymethoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza4-oxo-spiro[4,5]decane, a reaction product of 7,7,9,9-tetramethyl-2-cycloundecyl-1-oxa-3,8-diaza-4-oxospiro [4,5]decane und epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethyl phenyl)-1,3,5-triazine, 2-[2-hydroxy4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tertbutylphenyl)pentaerythritol diphosphite, tristearyl sorbitol triphosphite, tetrakis(2,4-di-tert- butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-12-methyl-dibenz[d,g]-1, 3,2-dioxaphosphocin, bis(2,4-di-tert-butyl-6-methylphenyl) methylphosphite, bis(2,4-di-tert-butyl-6methylphenyl) ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863, U.S. Pat. No. 4,338, 244, U.S. Pat. No. 5,175,312, U.S. Pat. No. 5,216,052, U.S. Pat. No. 5,252,643, DE-A-4316611, DE-A-4316622, DE-A-4316876, EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3, 5-dimethylphenyl)-5,7-di-tert-butyl-benzofuran-2-one, 3-(3, 5-dimethyl-4-pivaloyloxyphenyl)-5,7-di-tert-butyl-benzofuran-2-one.

The weight ratio of the product of the formula (I) to the conventional additives may be 1:0.5 to 1:5.

The product of the formula (I) can also be used as stabilizer, especially as light stabilizer, for almost all materials known in the art of photographic reproduction and other reproduction techniques as e.g. described in Research Disclosure 1990, 31429 (pages 474 to 480).

The invention is illustrated in more detail by the following Examples. All percentages and parts are by weight, unless otherwise indicated. Examples 1, 3, 4, 5 and 7 relate to a particularly preferred embodiment of the present invention.

GPC (Gel Permeation Chromatography) is used as an analytical procedure for separating molecules by their difference in size and to obtain molecular weight averages ($\overline{M}w$, $\overline{M}n$) or information on the molecular weight distribution of polymers.

The technique is well known and described, for instance, in "Modern Size—Exclusion Liquid Chromatography" by W. W. Yan et al., edited by J.Wiley & Sons, N.Y., USA, 1979, pages 4–8, 249–283 and 315–340.

A narrow molecular weight distribution is characterized by a polydispersity ($\overline{M}w/\overline{M}n$) close to 1.

The GPC analyses shown in the following Examples are carried out with a GPC chromatograph ®Perkin-Elmer LC 250 equipped with ®Perkin-Elmer RI detector LC 30 and with ®Perkin-Elmer oven LC 101.

All the analyses are carried out at 45° C. by using three columns PLGEL 3 μm Mixed E 300 mm length×7.5 mm i.d. (from Polymers Laboratories Ltd. Shropshire, U.K).

Tetrahydrofurane is used as eluant (flow 0.40 ml/min) and the samples are dissolved in tetrahydrofurane (2%) (% w/v).

In the structural formulae of the following examples, n' indicates that there are repetitive units in the molecules and the products obtained are not uniform. These products are characterized by the number average molecular weight $\overline{M}n$ and the polydispersity $\overline{M}w/\overline{M}n$.

EXAMPLE A

Preparation of the Compound of the Formula

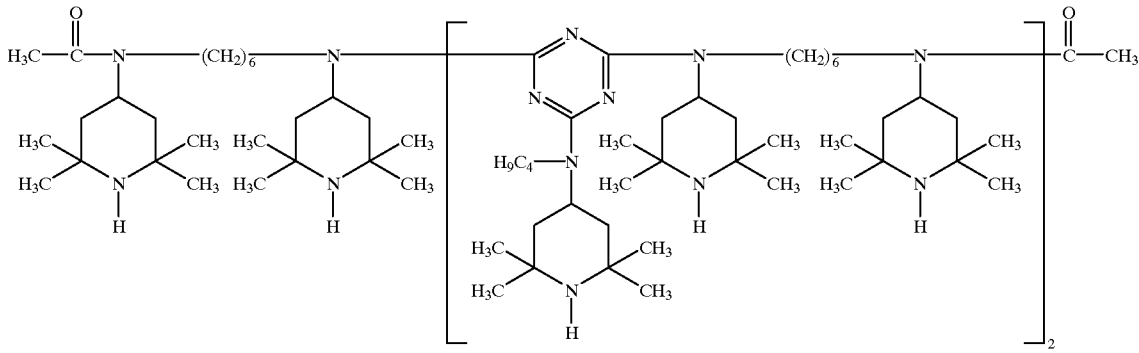

At 0° C., a solution of 74.3 g (0.35 moles) of N-(2,2,6,6-tetramethyl-4-piperidinyl)-n-butylamine in 50 ml of water is added slowly and under stirring to a solution of 64.5 g (0.35 moles) of cyanuric chloride in 500 ml of xylene.

Then, the mixture is stirred during 2 hours at room temperature and, after cooling to 0° C., an aqueous solution of 14.7 g (0.37 moles) of sodium hydroxide in 50 ml of water is added.

Subsequently, the aqueous solution is separated off and 69.2 g (0.175 moles) of N,N'-bis(2,2,6,6-tetramethyl-4-piperidinyl)-1,6-hexanediamine are added.

The mixture is heated to 50° C. for 1 hour. Then, 48.4 g (0.35 moles) of ground anhydrous potassium carbonate are added and the mixture is heated to 60° C. for 4 hours. After washing with water, the organic phase is concentrated (250 ml of xylene are recovered) and 1381 g (3.5 moles) of N,N'-bis-(2,2,6,6-tetramethyl-4-piperidinyl)-1,6-hexanediamine are added. After heating the mixture to 140° C. for 2 hours, 28 g (0.7 moles) of ground sodium hydroxide are added and the mixture is heated to reflux for 8 hours, being the water of the reaction distilled off azeotropically. 250 ml of xylene are added and the mixture is then filtered. The solution is concentrated under vacuum (140° C./1 mbar) and the excess of N,N'-bis(2,2,6,6-tetramethyl-4-piperidinyl)-1,6-hexanediamine is eliminated off under vacuum (190° C./0.2 mbar). The residue is taken up with 300 ml of xylene and 17.9 g (0.175 moles) of acetic anhydride are added.

Then, the mixture is heated to 130° C. for 5 hours. After cooling to room temperature, 34.6 g (0.25 moles) of ground potassium carbonate are added and the mixture is heated to 130° C. for 2 hours. The mixture is then cooled to 50° C., filtered and concentrated under vacuum at 140° C./1 mbar.

EXAMPLE 1

Preparation of the Product of the Formula

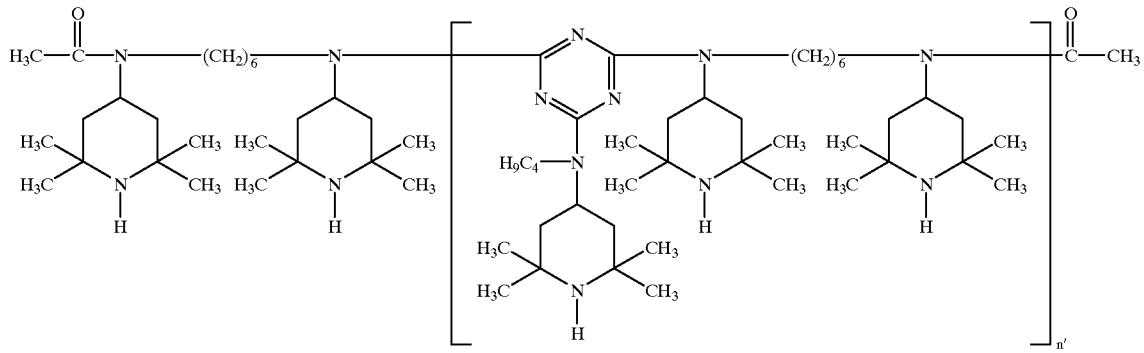

A solution of 37.1 g (0.175 moles) of N-(2,2,6,6-tetramethyl-4-piperidinyl)-n-butylamine in 30 ml of water is slowly added at 0° C. to a solution of 32.2 g (0.175 moles) of cyanuric chloride in 250 ml of xylene, keeping the temperature during the addition and for further 1 hour.

After 2 hours at room temperature, the mixture is cooled to 0° C. and an aqueous solution of 7.3 g (0.18 moles) of sodium hydroxide in 25 ml of water is added.

After ½ hour at 0° C. and further 2 hours at room temperature, the aqueous solution is separated off and 34.6 g (0.087 moles) of N,N'-bis[2,2,6,6-tetramethyl-4-piperidinyl]-1,6-hexanediamine are added.

The mixture is heated to 50° C. for 1 hour and 24.2 g (0.175 moles) of ground potassium carbonate are added and heated to 60° C. for 4 hours.

After washing with water, the organic phase is concentrated under vacuum at 60°–70° C./1 0 mbar, being 125 ml of xylene recovered.

69 g (0.175 moles) of N,N'-bis[2,2,6,6-tetramethyl-4-piperidinyl]-1,6-hexanediamine are added and the mixture is heated to 150° C. for 2 hours, cooled again and 7 g (0.175 moles) of ground sodium hydroxide are added.

The mixture is heated to 140° C. for further 4 hours, being the residual water of reaction eliminated off azeotropically, and for further 4 hours at 160° C.

After cooling to 60° C., the mixture is diluted with 130 ml of xylene, filtered and washed three times with 50 ml of ethylene glycol.

After concentrating under vacuum at 60° C./10 mbar, 7.5 g (0.073 moles) of acetic anhydride are added. After ½ hour at room temperature, the mixture is heated to 130° C. for 5 hours. After cooling to room temperature, 20.2 g (0.146 moles) of ground potassium carbonate are added and the mixture is heated to 130° C. for 2 hours.

Then, the mixture is cooled to 50° C., filtered and concentrated under vacuum at 140° C./1 mbar.

A solid with a melting point of 128°–134° C. is obtained after drying.

$\overline{Mn}$ (by GPC)=2712 g/mole
$\overline{Mw}/\overline{Mn}$=1.41
The GPC analysis shows a chromatogram as in FIG. 1.

EXAMPLES 2 TO 4

Following the procedure described in EXAMPLE 1, under the same reaction conditions and using the appropriate reagents, the following products of the formula

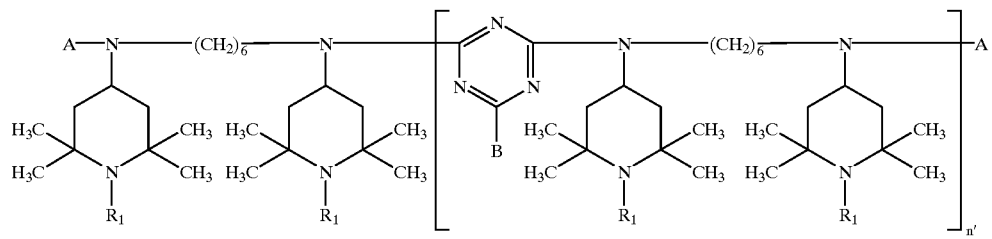

are prepared.

| Ex. | $R_1$ | A | B | melting point (° C.) | $\overline{Mn}$ | $\overline{Mw}/\overline{Mn}$ |
|---|---|---|---|---|---|---|
| 2 | —H | $H_5C_2$—NH—CO— | ![](piperidine with N—H, N-$H_9C_4$) | 122–130 | 2810 | 1.42 |
| 3 | —H | n-$H_9C_4$— | $H_3C{-}\underset{\underset{CH_3}{\mid}}{\overset{\overset{CH_3}{\mid}}{C}}{-}CH_2{-}\underset{\underset{CH_3}{\mid}}{\overset{\overset{CH_3}{\mid}}{C}}{-}NH{-}$ | 100–106 | 2760 | 1.34 |
| 4 | —H | $H_3C$—O—CO— | $(H_9C_4)_2N$— | 100–107 | 3095 | 1.40 |

Figure 2:
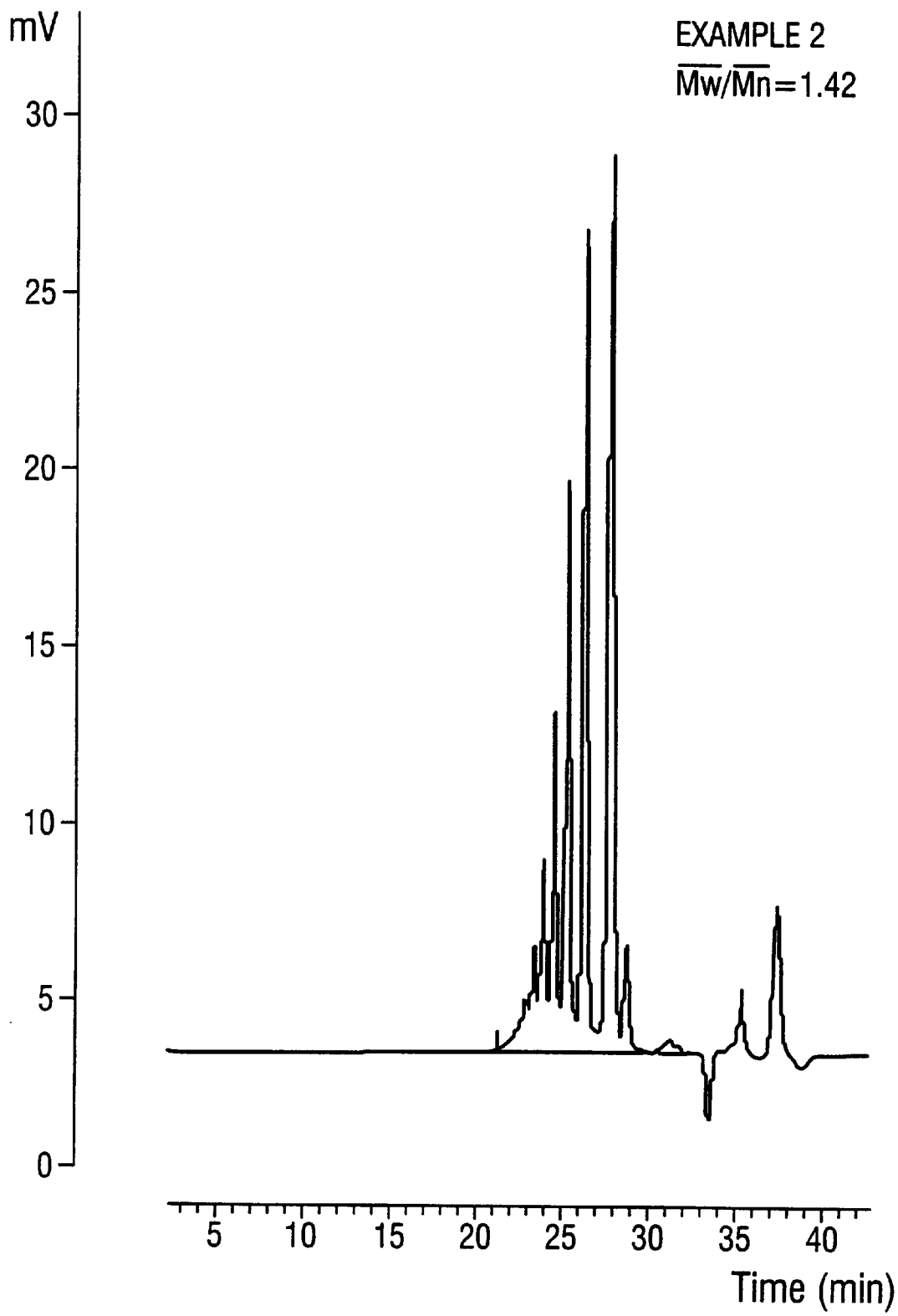
Figure 3:
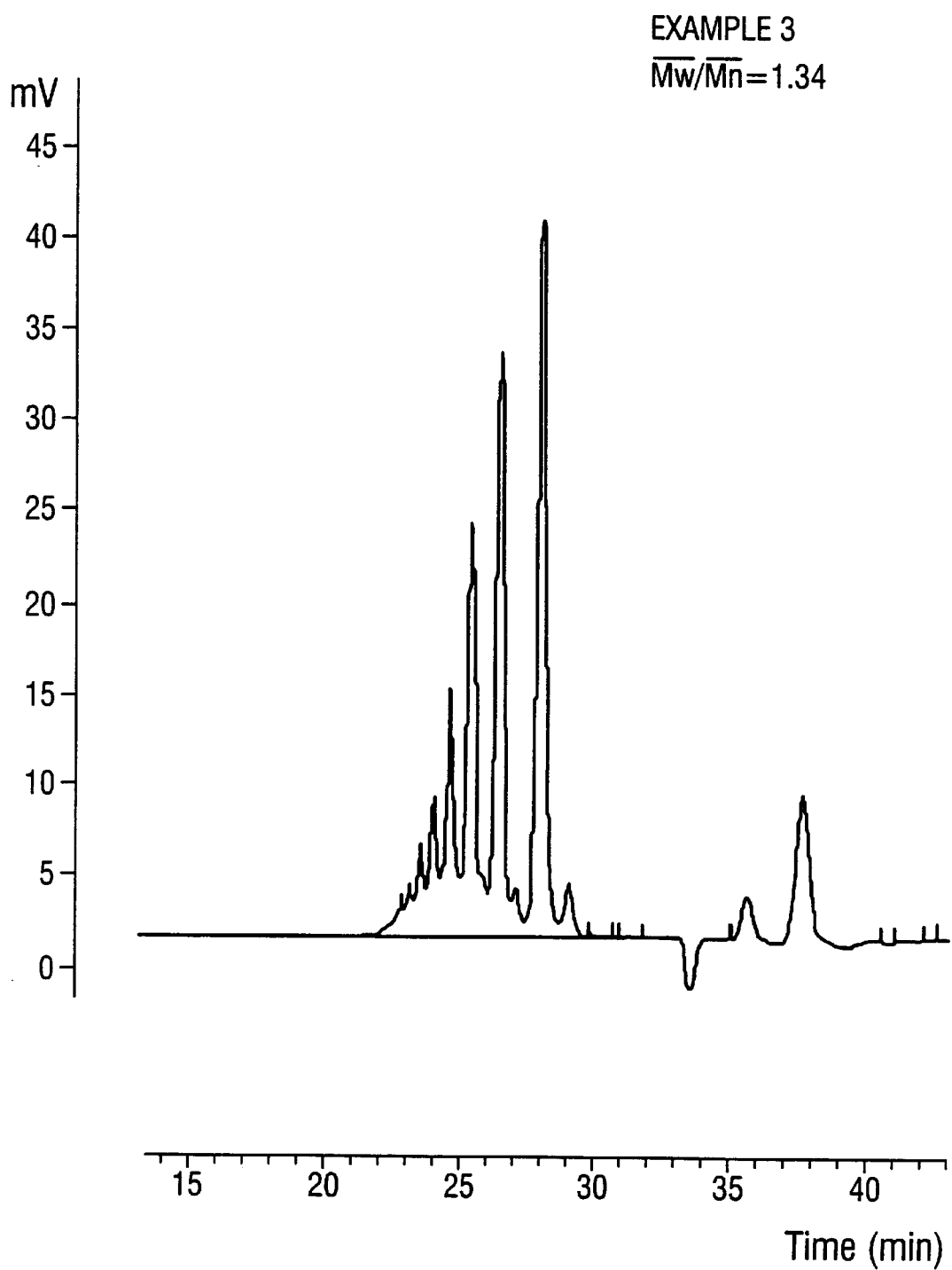
Figure 4:
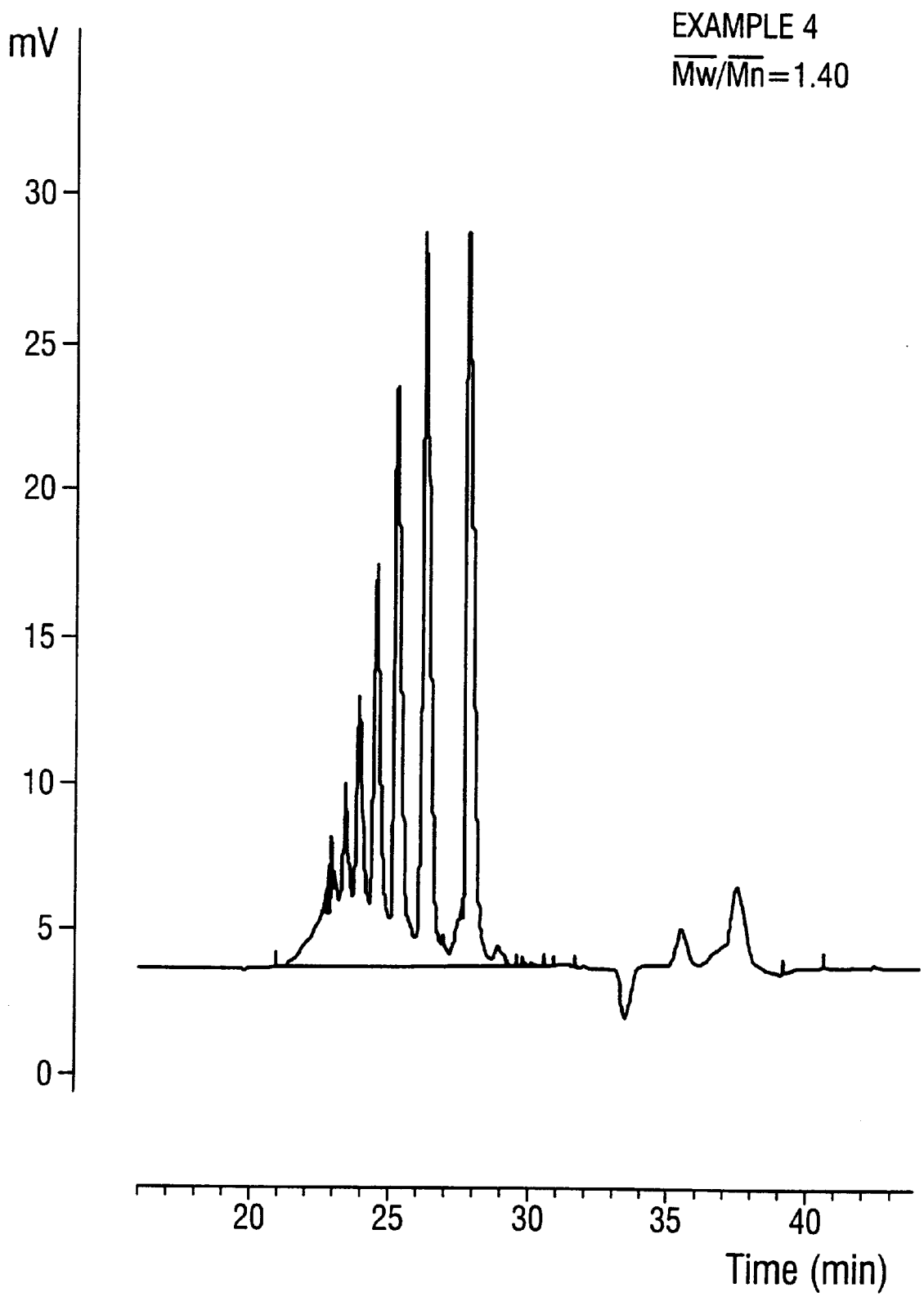

The GPC analysis of Examples 2 to 4 shows a chromatogram as in FIGS. 2 to 4.

EXAMPLE 5

Preparation of the Product of the Formula

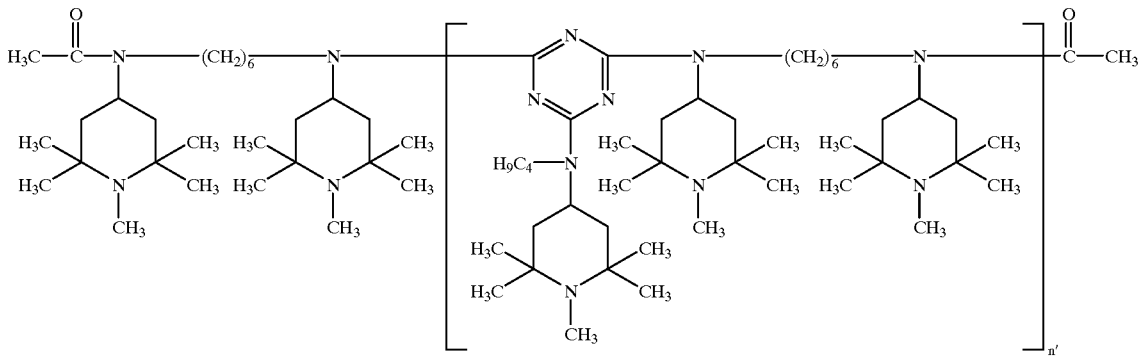

34.6 g (0.013 moles) of the product of EXAMPLE 1 are dissolved in an aqueous solution of 21 g (0.455 moles) of formic acid in 200 ml of water. 13.7 g (0.455 moles) of paraformaldehyde are added and the aqueous solution is heated under reflux for 16 hours.

After cooling to room temperature, 200 ml of xylene are added and, subsequently, 18.2 g (0.455 moles) of sodium hydroxide in 60 ml of water are added. After stirring for 2 hours, the organic phase is separated, washed with water and dried over sodium sulfate. After filtration, the organic phase is evaporated under vacuum at 140° C./10 mbar.

A solid with a melting point of 159°–163° C. is obtained after drying.

$\overline{Mn}$ (by GPC)=2920 g/mole $\overline{Mw}/\overline{Mn}$=1.40

Figure 5:
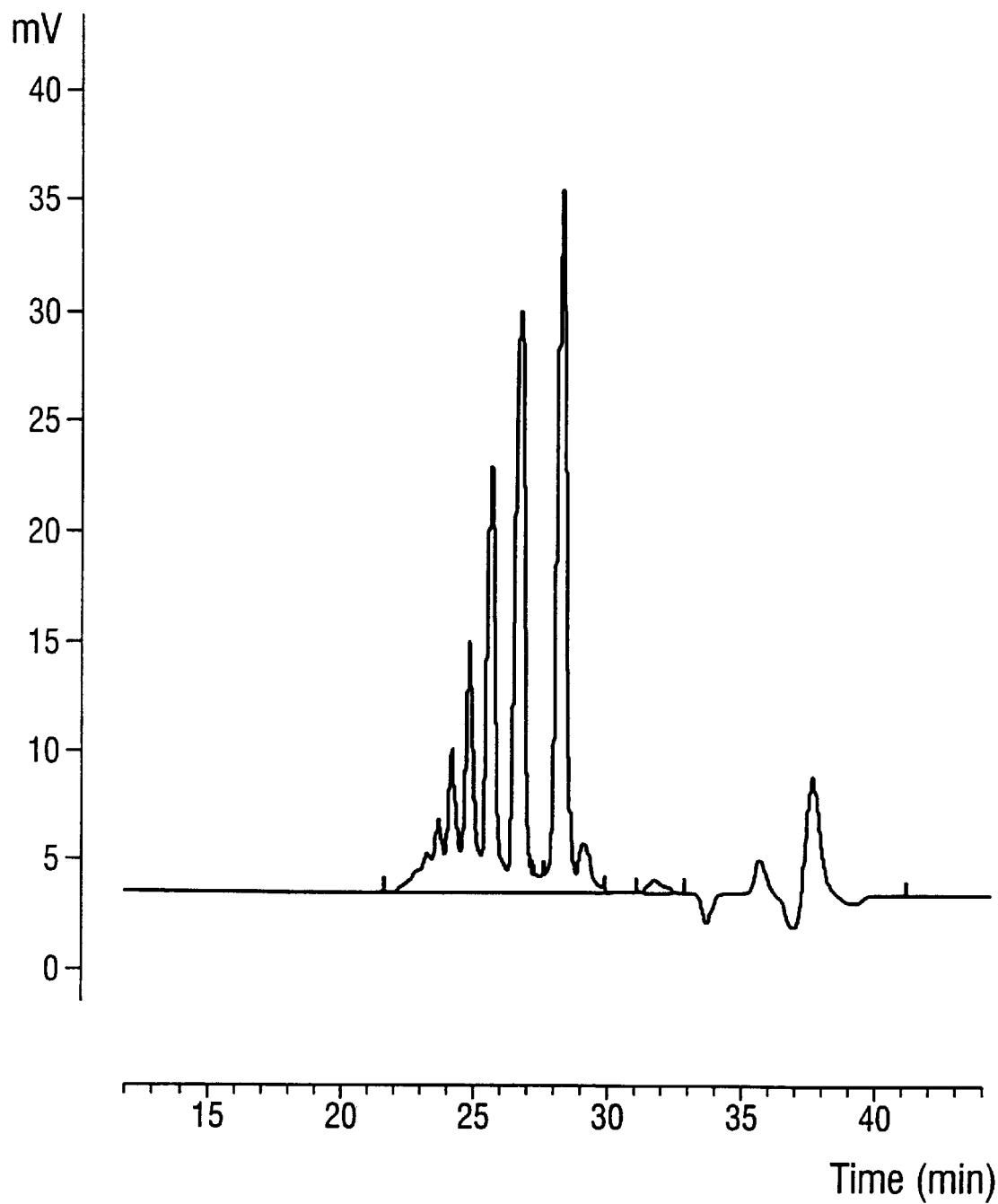

The GPC analysis shows a chromatogram as in FIG. 5.

EXAMPLE 6

A) Preparation of the product of the formula

The aqueous solution is then separated off and 34.6 g (0.087 moles) of N,N'-bis(2,2,6,6-tetramethyl-4-piperidinyl)-1,6-hexanediamine are added. The mixture is heated to 50° C. for 1 hour and 24.2 g (0.175 moles) of ground potassium carbonate are added and heated to 60° C. for 4 hours.

After washing with water, the organic phase is concentrated under vacuum at 60° C.–70° C./10 mbar, being 125 ml of xylene recovered.

69.0 g (0.175 moles) of N,N'-bis(2,2,6,6-tetramethyl-4-piperidinyl)-1,6-hexanediamine are added and the mixture is heated to 150° C. for 2 hours, cooled again and added with 7 g (0.175 moles) of ground sodium hydroxide.

The mixture is heated to 140° C. for further 4 hours, being the residual water of reaction eliminated off azeotropically and for further 4 hours at 160° C.

After cooling to 60° C., the mixture is diluted with 130 ml of xylene, filtered and washed three times with 50 ml of ethylene glycol.

Then, the solution is concentrated under vacuum at 60° C./1 mbar.

A solid with a melting point of 121°–128° C. is obtained after drying.

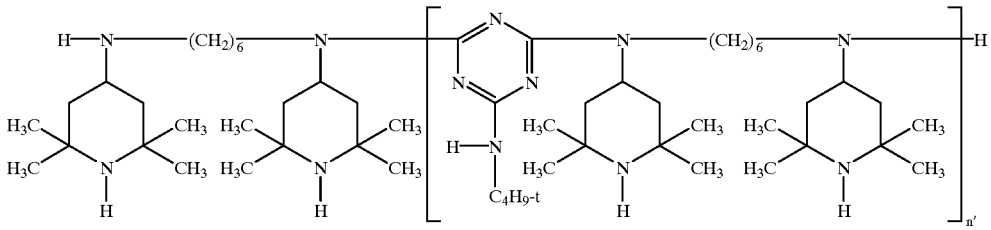

A solution of 12.8 g (0.175 moles) of t-butylamine in 20 ml of xylene is added slowly at 0° C. to a solution of 32.2 g (0.175 moles) of cyanuric chloride in 250 ml of xylene. Then, the mixture is heated to room temperature.

After 2 hours at room temperature, the mixture is cooled to 0° C. and an aqueous solution of 7.3 g (0.18 moles) of sodium hydroxide in 25 ml of water is added.

$\overline{Mn}$ (by GPC)=2475 g/mole $\overline{Mw}/\overline{Mn}$=1.34

Figure 6A:
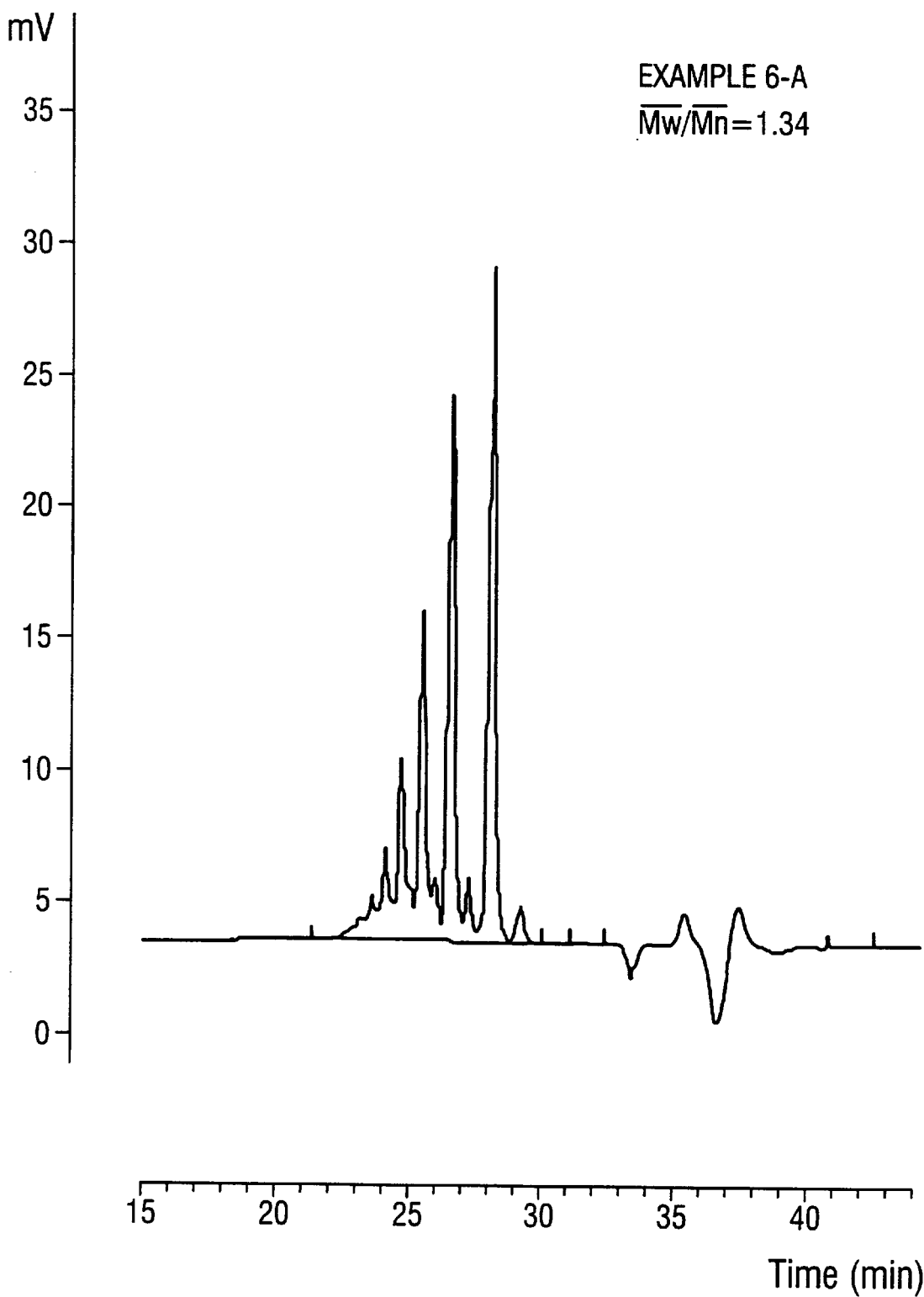

The GPC analysis shows a chromatogram as in FIG. 6A.

B) Following the procedure described in EXAMPLE 5, under the same reaction conditions and using the appropriate reagents, the product of the formula

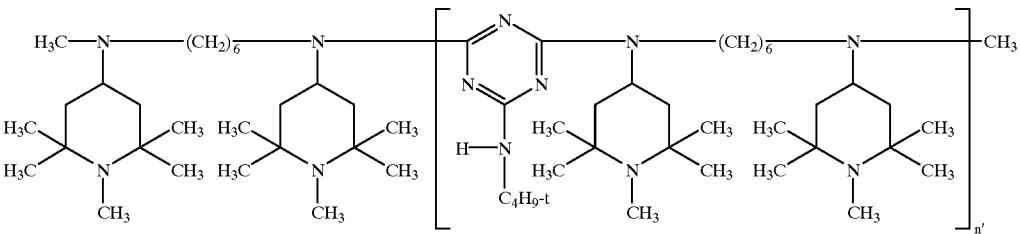

is prepared.

Figure 6B:
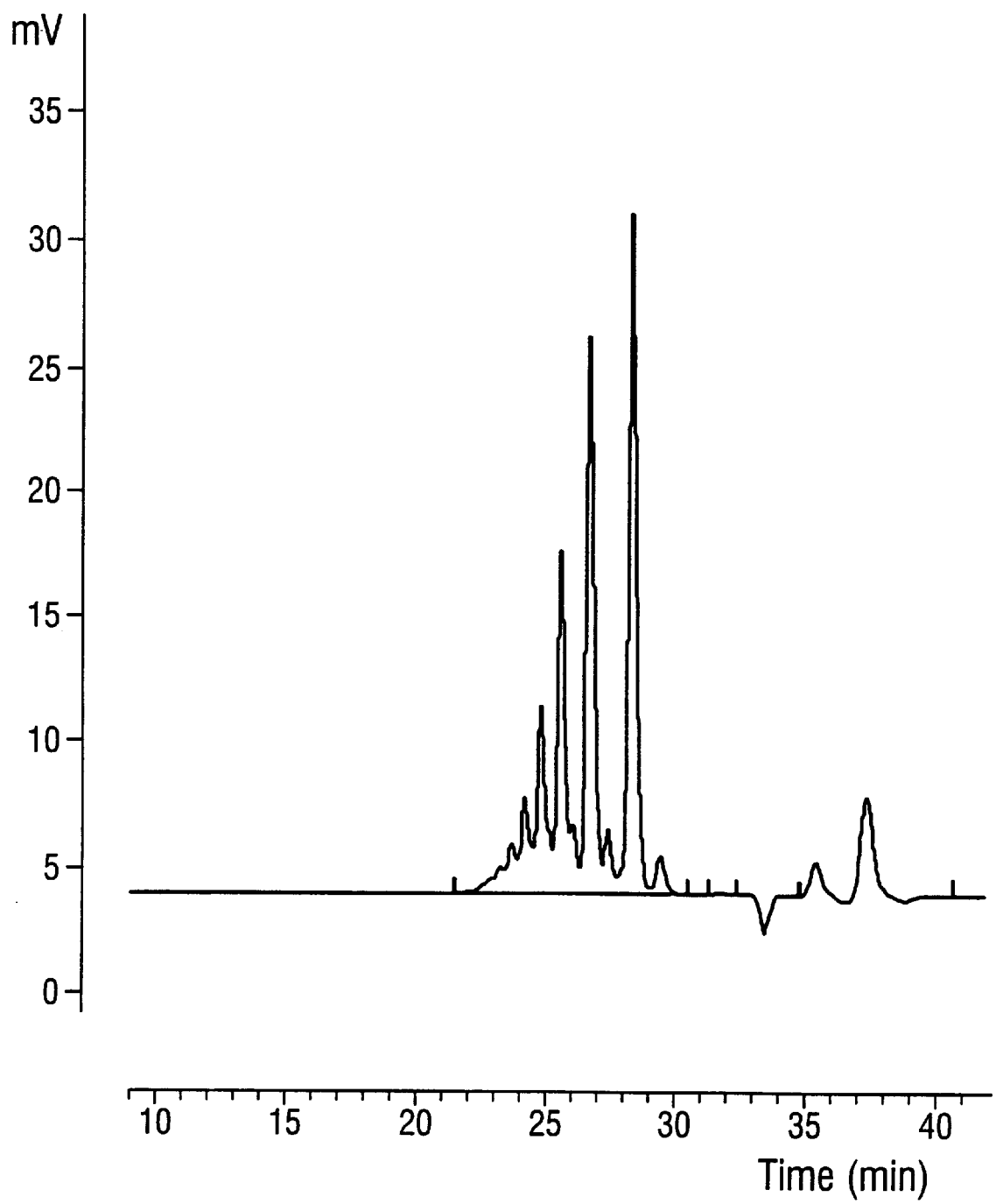

A solid with a melting point of 132°–140° C. is obtained.
$\overline{Mn}$ (by GPC)=2275 g/mole
$\overline{Mw}/\overline{Mn}$=1.35
The GPC analysis shows a chromatogram as in FIG. 6B.

EXAMPLE 7

Following the procedure described in EXAMPLE 5, under the same reaction conditions and using the appropriate reagents, the product of the formula

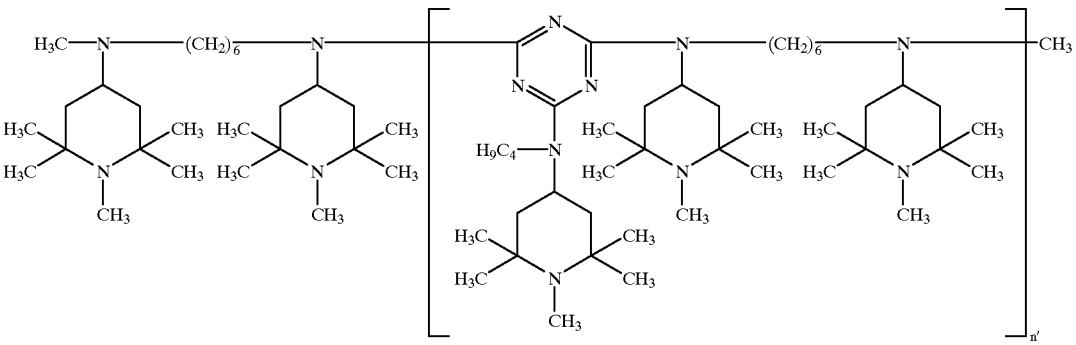

is prepared.

A solid with a melting point of 149°–156° C. is obtained after drying.
$\overline{Mn}$ (by GPC)=2518 g/mole
$\overline{Mw}/\overline{Mn}$=1.38
The GPC analysis shows a chromatogram as in FIG. 7.

The ratio of the three main single (monodispers) components ((n'=2):(n'=4):(n'=6)) of the polydispers product obtained according to the above EXAMPLE 1 is 2:0.93:0.4 and the ratio of the three main single (monodispers) components ((n'=2):(n'=4):(n'=6)) of the polydispers product obtained according to the above EXAMPLE 2 is 2:0.84:0.32.

EXAMPLE I

Light-stabilizing Action in Polypropylene Fibres 2.5 g of the stabilizer shown in Table 1, 1 g of tris(2,4-di-t-butylphenyl) phosphite, 1 g of calcium monoethyl 3,5-di-t-butyl-4-hydroxybenzyl-phosphonate, 1 g of calcium stearate and 2.5 g of titanium dioxide are mixed in a slow mixer with 1000 g of polypropylene powder having a melt index=12 g/10 min (measured at 230° C. and 2.16 kg).

The mixtures are extruded at 200–230° C. to obtain polymer granules which are then converted into fibres using a pilot-type apparatus (®Leonard-Sumirago(VA), Italy) and operating under the following conditions:

Extruder temperature: 230–245° C.
Head temperature: 255–260° C.
Draw ratio: 1:3.5
Linear density: 11 dtex per filament The fibres prepared in this way are exposed, after mounting on white cardboard, in a 65WR Weather-O-Meter (ASTM D2565-85) with a black panel temperature of 63° C.

For samples taken after various times of exposure to the light, the residual tenacity is measured using a constant-speed tensometer, and the exposure time in hours needed to halve the initial tenacity ($T_{50}$) is then calculated.

For purposes of comparison, fibres prepared under the same conditions as stated above, but without adding the stabilizers of the present invention, are also exposed.

The results are shown in Table 1.

TABLE 1

| Stabilizer | $T_{50}$ (hours) |
|---|---|
| compound of EXAMPLE 1 | 4040 |
| compound of EXAMPLE 7 | 3570 |

EXAMPLE II

Light-stabilizing Action in Polypropylene Tapes 1 g of each of the compounds listed in Table 2, 1 g of tris[2,4-di-tert-butylphenyl]phosphate, 0.5 g of pentaerythritol tetrakis[3-(3,5-di-tert-butyl-4-hydroxyphenyl) propionate] and 1 g of calcium stearate are mixed in a turbomixer with 1000 g of polypropylene powder having a melt index of 2.1 (measured at 230° C. and 2.16 Kg).

The mixtures are extruded at 200–220° C. to give polymer granules which are subsequently converted to stretched tapes of 50 μm thickness and 2.5 mm width, using a semi-industrial type of apparatus (®Leonard-Sumirago (VA)—Italy) and working under the following conditions:

Extruder temperature: 210–230° C.
Head temperature: 240–260° C.
Stretch ratio: 1:6

The tapes thus prepared are mounted on a white card and exposed in a Weather-O-Meter 65 WR (ASTM D 2565-85) with a black panel temperature of 63° C.

The residual tenacity is measured, by means of a constant velocity tensometer, on a sample taken after various light exposure times; from this, the exposure time (in hours) required to halve the initial tenacity ($T_{50}$) is measured.

By way of comparison, tapes prepared under the same conditions as indicated above, but without the addition of the stabilizers of the present invention, are exposed.

The results obtained are shown in Table 2.

TABLE 2

| Stabilizer | $T_{50}$ (hours) |
| --- | --- |
| compound of EXAMPLE 1 | 3110 |
| compound of EXAMPLE 7 | 2060 |

EXAMPLE III

Pigment Interaction in Polypropylene Plaques 5.625 g of the stabilizers shown in Table 3, 13.500 g of ®Pigment Blue 15 'Flush' (50% mixture in polyethylene) and 25.875 g of polypropylene powder having a melt index=14 gl/min (measured at 230° C. and 2.16 kg) are added to fill a ®Haake internal mixer at room temperature (®Haake Buchler Rheochord System 40 using a 60 cc 3 piece ®Rheomixer with cam blades). The cam blades are rotating at 5 rpm (revolutions per minute). A ram closes the bowl under a weight of 5 kg. The temperature is increased to 180° C. and is held.

The mixture is removed, while at 180° C., after 30 minutes and is cooled down to room temperature. The mixture so obtained is called the 'concentrate'.

0.900 g of the 'concentrate', 3.600 g of titanium dioxide 'Flush' (50% mixture in polyethylene) and 40.500 g of polypropylene powder having a melt index=14 g/min (measured at 230° C. and 2.16 kg) are added to a ®Haake mixer bowl at 160° C. The cam blades are rotating at 20 rpm. A ram closes the bowl under a weight of 5 kg. The temperature is increased to 170° C. and the rotating is increased to 125 rpm.

The molten mixture is removed at 170° C. after 30 minutes, is transferred to a hand held tool at room temperature and is transformed into a round plaque of 1 mm×25 mm in diameter. The mixture so obtained is called the 'letdown' and the plaque is called the 'letdown plaque'.

The color difference ΔE (CIE color difference equation) of the sample 'letdown plaque' containing the stabilizer indicated in Table 3 versus the control 'letdown plaque' without the stabilizer is measured. The measurement is done using an ®Applied Color Systems Spectrophotometer Model CS-5 (USA). The measurement parameters used are 400–700 nm-scan, small area view, reflectance, illuminate D65, 10 degree observer.

The above processing conditions are designated to simulate the manufacture of concentrates (masterbatches) of pigments and stabilizers and the subsequent 'let-down' (dilution) into finished plastic articles.

The results are shown in Table 3. A high ΔE indicates pigment agglomeration and poor dispersion. ΔE of 0.5 or less cannot be seen by the eye.

TABLE 3

| Stabilizer | ΔE |
| --- | --- |
| compound of EXAMPLE 4 | 1.0 |
| compound of EXAMPLE 7 | 1.5 |

EXAMPLE IV

Effect on Discoloration of Polypropylene Plaques 1 g of each of the stabilizers listed in Table 4 and 1 g of calcium stearate are mixed in a turbomixer with 1000 g of polypropylene powder having a melt index=2 g/min (measured at 230° C. and 2.16 kg) and already stabilized with 1 g of tris[2,4-di-tert-butylphenyl] phosphite and 1 g of pentaerythritol tetrakis[3-(3,5-di-tert-butyl-4-hydroxyphenyl) propionate].

The mixture is extruded at 200°–220° C. to give polymer granules which are subsequently converted into 1 mm thick plaques, using a compression bench press ®PASADENA P 210 C (®Pasadena-USA) and working under the following conditions:

Temperature: 230° C.
Pressure: 20.000 lbs
Time under pressure: 6'
Cooling: in cold water The plaques thus prepared are exposed in a forced circulating air oven for 7 days at 120° C.

After the oven exposure, the Yellowness Index (YI) of the plaques is measured with a chromaticity meter ®MINOLTA CR 210.

The results obtained are shown in Table 4.

TABLE 4

| Stabilizer | YI |
| --- | --- |
| compound of EXAMPLE 5 | 13.3 |
| compound of EXAMPLE 6 B | 13.1 |
| compound of EXAMPLE 7 | 14.0 |

What is claimed is:

1. A mixture containing at least three different compounds of the formula (I), which vary only by the variable n, said mixture having a polydispersity $\overline{M}w/\overline{M}n$ of 1.1 to 1.5;

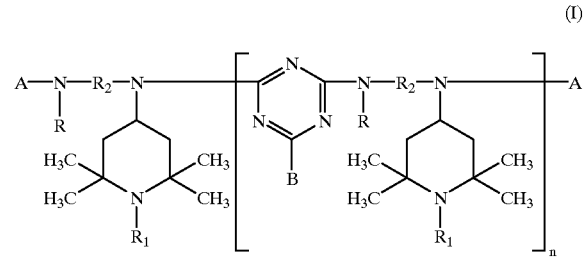

wherein n is 2, 3, 4, 5, 6, 7, 8, 9, 10, 11, 12, 13 or 14;

the radicals $R_1$ are independently of one another hydrogen, $C_1$–$C_8$alkyl, $C_1$–$C_8$hydroxyalkyl, —$CH_2CN$, $C_3$–$C_6$alkenyl, $C_3$–$C_6$alkynyl, $C_7$–$C_9$phenylalkyl which is unsubstituted or substituted on the phenyl by 1, 2 or 3 $C_1$–$C_4$alkyl; $C_1$–$C_8$acyl, ($C_1$–$C_8$alkoxy)carbonyl or ($C_5$–$C_{12}$cycloalkoxy) carbonyl;

$R_2$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N-$X_1$ with $X_1$ being $C_1$–$C_{12}$acyl or ($C_1$–$C_{12}$alkoxy)carbonyl or having one of the definitions of $R_4$ given below except hydrogen; or $R_2$ is a group of the formula (a), (b) or (c);

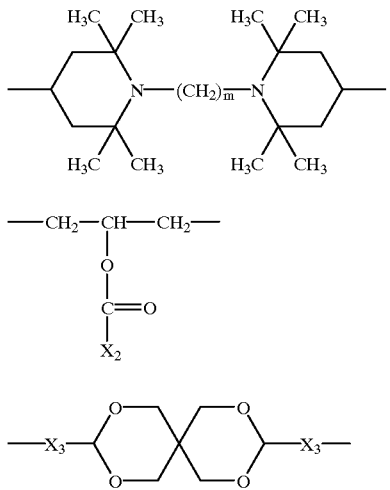

(a)

(b)

(c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another $C_1$–$C_8$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aninocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$;

B is $OR_3$, —$N(R_4)(R_5)$ or a group of the formula (II);

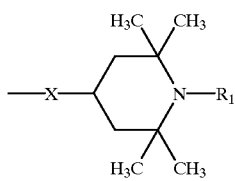

(II)

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

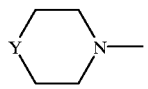

(III)

with Y being —O—, —$CH_2$—, —$CH_2CH_2$— or >N—$CH_3$, or —$N(R_4)(R_5)$ is additionally a group of the formula (III);

X is —O— or >N-$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

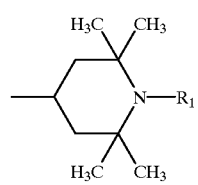

(IV)

or $C_2$–$C_4$alkyl which is substituted in the 2, 3 or 4 position by —OH, $C_1$–$C_8$alkoxy, di($C_1$–$C_4$alkyl)amino or a group of the formula (III); and R has one of the meanings given for $R_6$;

with the proviso that in the individual recurrent units of the formula (I), each of the radicals B, R, $R_1$ and $R_2$ has the same or a different meaning.

2. A mixture according to claim 1, wherein R is a group of the formula (IV).

3. A mixture according to claim 1, wherein the radicals $R_1$ are independently of one another hydrogen, $C_1$–$C_4$alkyl, allyl, benzyl or acetyl.

4. A mixture according to claim 1, wherein $R_2$ is $C_2$–$C_{12}$alkylene, $C_5$–$C_7$cycloalkylene, $C_5$–$C_7$cycloalcylenedi($C_1$–$C_4$alkylene), $C_1$–$C_4$alkylenedi($C_5$–$C_7$cycloalkylene) or phenylenedi($C_1$–$C_4$alkylene); the radicals A are independently of one another $C_1$–$C_8$acyl, ($C_1$–$C_8$alkoxy)carbonyl, ($C_5$–$C_7$cycloalkoxy)carbonyl, ($C_1$–$C_4$alkyl)aminocarbonyl, ($C_5$–$C_7$cycloallyl)aminocarbonyl, benzylaminocarbonyl, $C_1$–$C_6$alkyl, $C_5$–$C_7$cycloalkyl, allyl or benzyl;

$R_3$, $R_4$ and $R_5$, which are identical or different, are hydrogen, $C_1$–$C_{12}$allyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (III); or —$N(R_4)(R_5)$ is additionally a group of the formula (III); and $R_6$ is hydrogen, $C_1$–$C_{12}$alkyl, $C_5$–$C_7$cycloalkyl which is unsubstituted or substituted by 1, 2 or 3 $C_1$–$C_4$alkyl;

benzyl which is unsubstituted or substituted on the phenyl by 1, 2 or 3 $C_1$–$C_4$alkyl; tetrahydrofurfuryl, a group of the formula (IV) or $C_2$–$C_3$alkyl which is substituted in the 2 or 3 position by —OH, $C_1$–$C_4$alkoxy, di($C_1$–$C_4$alkyl)amino or a group of the formula (III).

5. A mixture according to claim 1, wherein $R_2$ is $C_2$–$C_8$alkylene;

the radicals A are independently of one another $C_1$–$C_8$acyl, ($C_1$–$C_8$alkoxy)carbonyl, cyclohexoxycarbonyl, ($C_1$–$C_4$alkyl)aminocarbonyl, cyclohexylaminocarbonyl, benzylaminocarbonyl, $C_1$–$C_4$alkyl, cyclohexyl, allyl or benzyl;

$R_3$, $R_4$ and $R_5$, which are identical or different, are hydrogen, $C_1$–$C_9$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —N($R_4$)($R_5$) is additionally 4-morpholinyl; and $R_6$ is hydrogen, $C_1$–$C_8$alkyl, cyclohexyl which is unsubstituted or substituted by methyl; benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

6. A mixture according to claim 1, wherein n is 2, 3, 4, 5 or 6;

the radicals $R_1$ are independently of one another hydrogen or methyl;

$R_2$ is $C_2$–$C_6$alkylene;

the radicals A are independently of one another $C_1$–$C_8$acyl, ($C_1$–$C_8$alkoxy)carbonyl, ($C_1$–$C_4$alkyl)aminocarbonyl, $C_1$–$C_4$alkyl or allyl;

the radicals B are independently of one another —N($R_4$)($R_5$) or a group of the formula (II);

$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl;

X is >$NR_6$; and $R_6$ is $C_1$–$C_4$allyl.

7. A mixture according to claim 1, wherein A is acetyl, ($C_1$–$C_2$alkoxy)carbonyl, ($C_1$–$C_2$alkyl)aminocarbonyl or $C_1$–$C_4$alkyl.

8. A mixture according to claim 1, wherein formula (I) corresponds to

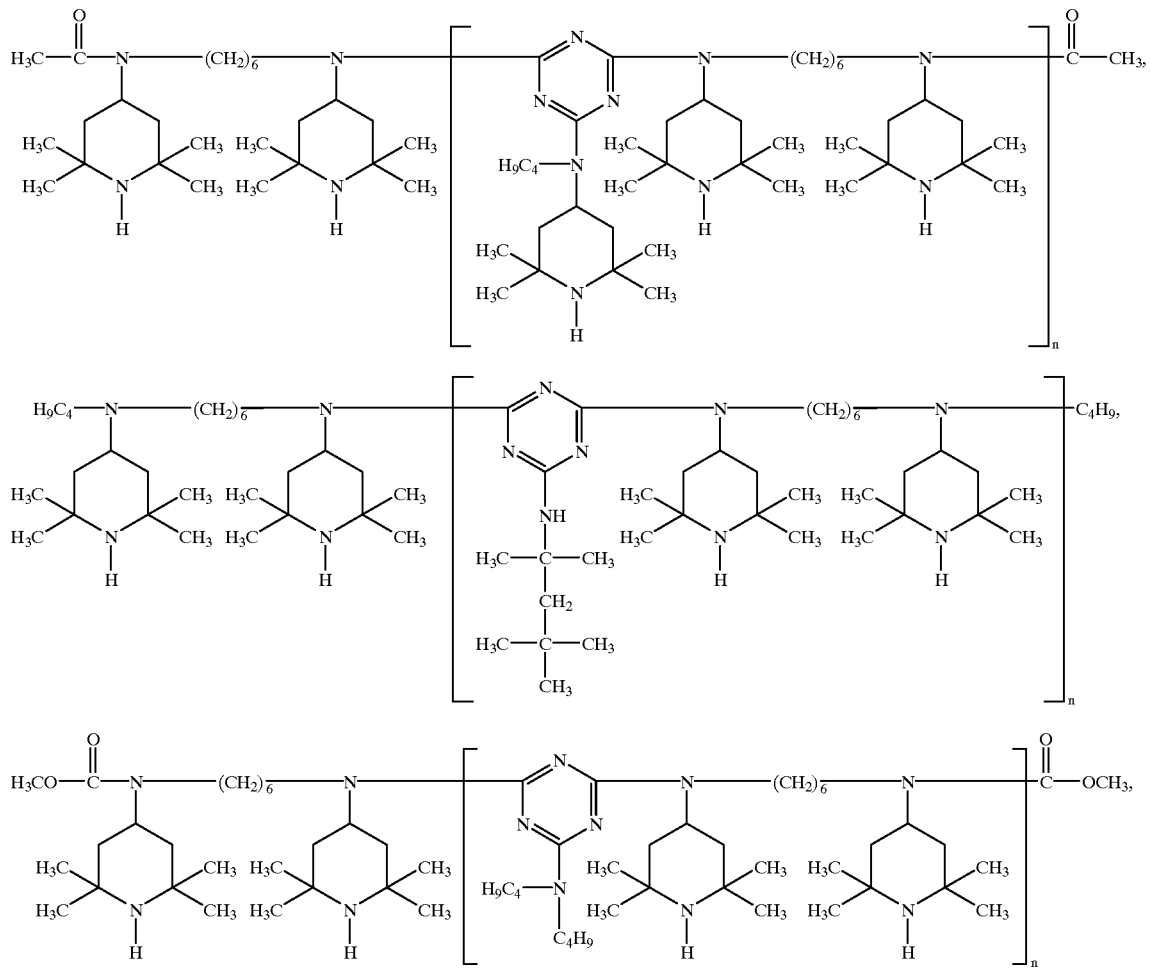

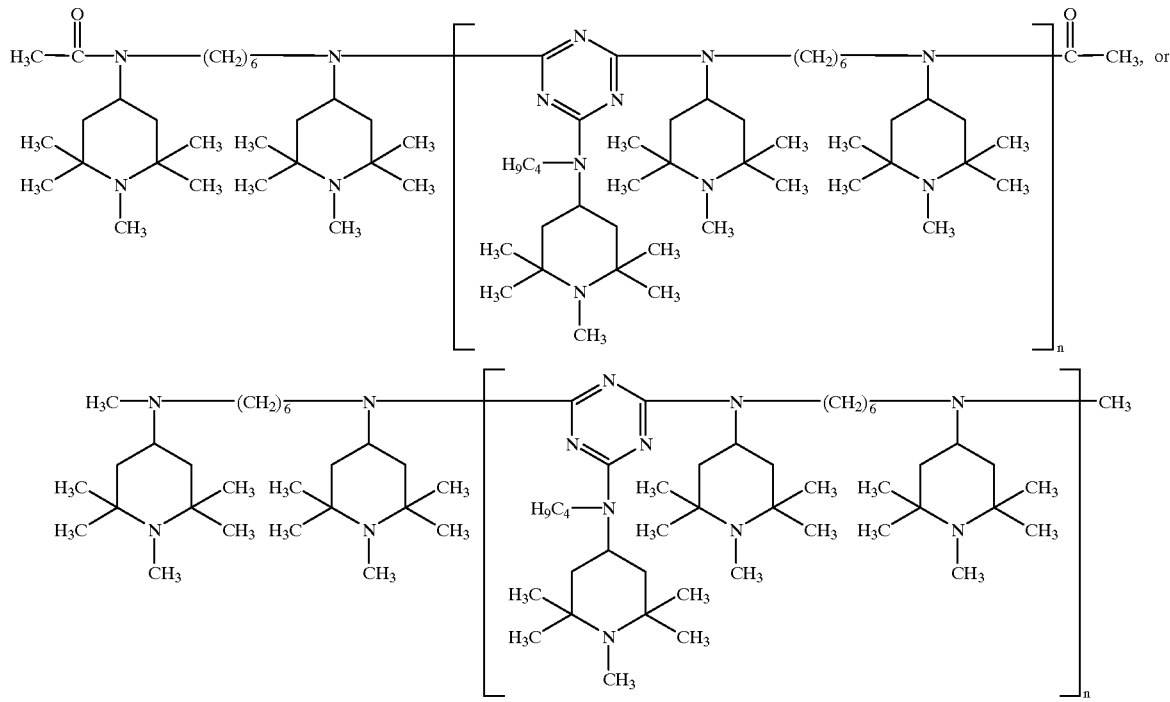

wherein n is 2, 3, 4, 5, 6, 7, 8, 9, 10, 11, 12, 13 or 14.

9. A mixture according to claim 1, containing a) a monodisperse compound of the formula (Ia),

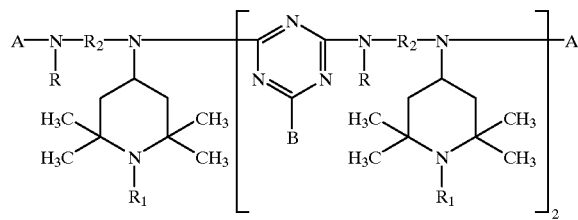

(Ia)

b) a monodisperse compound of the formula (Ib) and

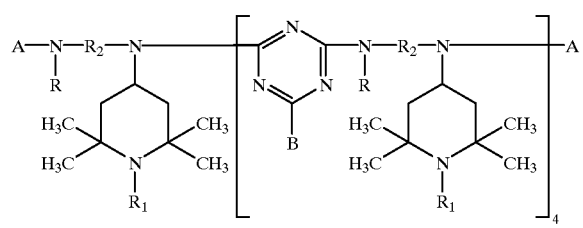

(Ib)

c) a monodisperse compound of the formula (Ic)

(Ic)

wherein A, B, R, $R_1$ and $R_2$ are in the formulae (Ia), (Ib) and (Ic) identical and are as defined in claim 1, and the molar ratio of the monodisperse compounds of the formula (Ia) to (Ib) to (Ic) is 2:2:1.5 to 2:0.5:0.05.

10. A mixture according to claim 9, wherein the molar ratio of the monodisperse compounds of the formula (Ia) to (Ib) to (Ic) is 2:1.5:1 to 2:0.5:0.08.

11. A mixture according to claim 9, wherein the radicals $R_1$ are independently of one another hydrogen or methyl;

$R_2$ is $C_2$–$C_6$alkylene;

A is acetyl, ($C_1$–$C_2$alkoxy)carbonyl, ($C_1$–$C_2$alkyl) aminocarbonyl or $C_1$–$C_4$alkyl;

B is —N($R_4$)($R_5$) or a group of the formula (II) with $R_1$ being as defined above;

$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl;

X is >NR$_6$;

R$_6$ is C$_1$–C$_4$alkyl; and

R is a group of the formula (IV) with R$_1$ being as defined above.

12. A composition containing an organic material susceptible to degradation induced by light, heat or oxidation and a mixture according to claim 1, with the proviso that the totality of the compounds of formula (I) present in the composition has a polydispersity $\overline{Mw}/\overline{Mn}$ of 1.1 to 1.5.

13. A composition according to claim 12, wherein the organic material is a synthetic polymer.

14. A composition according to claim 12, wherein the organic material is polyethylene or polypropylene.

15. A method for stabilizing an organic material against degradation induced by light, heat or oxidation, which comprises incorporating into said organic material a mixture according to claim 1, with the proviso that the totality of the compounds of formula (I) present in the organic material has a polydispersity $\overline{Mw}/\overline{Mn}$ of 1.1 to 1.5.

16. A mixture, having a polydispersity Mw/Mn of 1.1 to 1.5, obtainable by 1) reacting a compound of the formula (A)

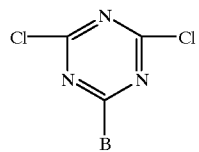

(A)

with a compound of the formula (B)

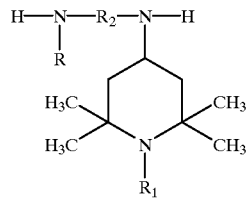

(B)

in a stoichiometric ratio to obtain a compound of the formula (C);

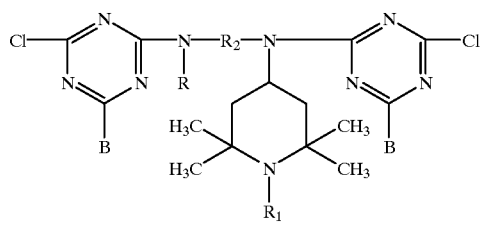

(C)

2) reacting a compound of the formula (C) with a compound of the formula (B) in a molar ratio of 1:2 to 1:3, to obtain a mixture of at least three different compounds of the formula (D) with n being 2, 3, 4, 5, 6, 7, 8, 9, 10, 11, 12, 13 or 14;

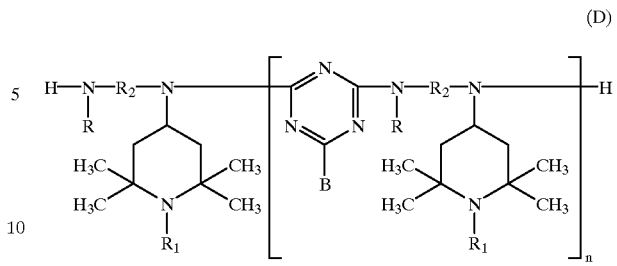

(D)

3) reacting the mixture obtained in 2) with a compound of the formula (E) or with a compound of the formula (F)

A'-X'  (E)

A"-NCO  (F)

wherein X' is a leaving group;

A' is C$_1$–C$_8$acyl, (C$_1$–C$_8$alkoxy)carbonyl, (C$_5$–C$_{12}$cycloalkoxy)carbonyl, C$_1$–C$_8$alkyl, C$_5$–C$_{12}$cycloalkyl which is unsubstituted or substituted by 1, 2 or 3 C$_1$–C$_4$alkyl; C$_3$–C$_6$alkenyl, C$_7$–C$_9$phenylalkyl which is unsubstituted or substituted on the phenyl by 1, 2 or 3 C$_1$–C$_4$alkyl; or —CH$_2$CN; and A" is C$_1$–C$_8$alkyl, C$_5$–C$_{12}$cycloalkyl or C$_7$–C$_9$phenylalkyl;

in about a stoichiometric ratio to obtain the mixture;

the reactions 1) to 3) being carried out in an organic solvent in the presence of an inorganic base with the proviso that, when in the reaction 3) a compound of the formula (F) is applied, said reaction 3) is carried out without any inorganic base;

the radicals R$_1$ are independently of one another hydrogen, C$_1$–C$_8$alkyl, C$_1$–C$_8$hydroxyalkyl, —CH$_2$CN, C$_3$–C$_6$alkenyl, C$_3$–C$_6$alkynyl, C$_7$–C$_9$phenylalkyl which is unsubstituted or substituted on the phenyl by 1, 2 or 3 C$_1$–C$_4$alkyl; C$_1$–C$_8$acyl, (C$_1$–C$_8$alkoxy)carbonyl or (C$_5$–C$_{12}$cyclo-alkoxy)carbonyl;

R$_2$ is C$_2$–C$_{12}$alkylene, C$_4$–C$_{12}$alkenylene, C$_5$–C$_7$cycloalkylene, C$_5$–C$_7$cycloalkylene-di(C$_1$–C$_4$alkylene), C$_1$–C$_4$alkylenedi(C$_5$–C$_7$cycloalkylene), phenylenedi(C$_1$–C$_4$alkylene) or C$_4$–C$_{12}$alkylene interrupted by 1,4-piperazinediyl, —O— or >N-X$_1$ with X$_1$ being C$_1$–C$_{12}$acyl or (C$_1$–C$_{12}$alkoxy)carbonyl or having one of the definitions of R$_4$ given below except hydrogen; or R$_2$ is a group of the formula (a), (b) or (c);

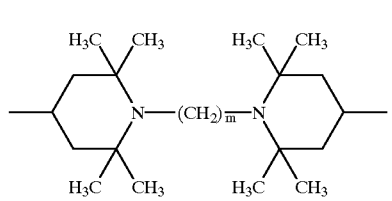

(a)

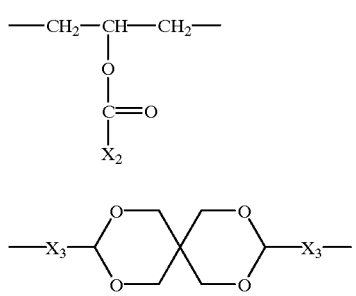
(b)

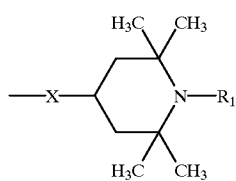
(c)

with m being 2 or 3,

X$_2$ being C$_1$–C$_{18}$alkyl, C$_5$–C$_{12}$cycloalkyl which is unsubstituted or substituted by 1, 2 or 3 C$_1$–C$_4$alkyl; phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; and the radicals X$_3$ being independently of one another C$_2$–C$_{12}$alkylene;

B is OR$_3$, —N(R$_4$)(R$_5$) or a group of the formula (II);

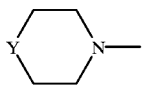
(II)

R$_3$, R$_4$ and R$_5$, which are identical or different, are hydrogen, C$_1$–C$_{18}$alkyl, C$_5$–C$_{12}$cycloalkyl which is unsubstituted or substituted by 1, 2 or 3 C$_1$–C$_4$alkyl; C$_3$–C$_{18}$alkenyl, phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; tetrahydrofurfuryl or C$_2$–C$_4$alkyl which is substituted in the 2, 3 or 4 position by —OH, C$_1$–C$_8$alkoxy, di(C$_1$–C$_4$alkyl)amino or a group of the formula (III);

(III)

with Y being —O—, —CH$_2$—, —CH$_2$CH$_2$— or >N—CH$_3$, or —N(R$_4$)(R$_5$) is additionally a group of the formula (III);

X is —O— or >N-R$_6$;

R$_6$ is hydrogen, C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (IV),

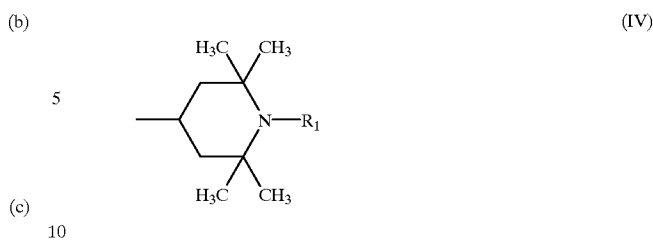
(IV)

or C$_2$–C$_4$alkyl which is substituted in the 2, 3 or 4 position by —OH, C$_1$–C$_8$alkoxy, di(C$_1$–C$_4$alkyl)amino or a group of the formula (III); and R has one of the meanings given for R$_6$;

with the proviso that in the individual recurrent units of the formula (I), each of the radicals B, R, R$_1$ and R$_2$ has the same or a different meaning.

17. A mixture according to claim 16, wherein R is a group of the formula (IV).

18. A mixture according to claim 16, wherein the radicals R$_1$ are independently of one another hydrogen, C$_1$–C$_4$alkyl, allyl, benzyl or acetyl.

19. A mixture according to claim 16, wherein

R$_2$ is C$_2$–C$_{12}$alkylene, C$_5$–C$_7$cycloalkylene, C$_5$–C$_7$cycloalkylenedi(C$_1$–C$_4$alkylene), C$_1$–C$_4$alkylenedi(C$_5$–C$_7$cycloalkylene) or phenylenedi(C$_1$–C$_4$alkylene);

A' is C$_1$–C$_8$acyl, (C$_1$–C$_8$alkoxy)carbonyl, (C$_5$–C$_7$cycloalkoxy)carbonyl, C$_1$–C$_6$alkyl, C$_5$–C$_7$cycloalkyl, allyl or benzyl;

A" is C$_1$–C$_4$alkyl, C$_5$–C$_7$cycloalkyl or benzyl;

R$_3$, R$_4$ and R$_5$, which are identical or different, are hydrogen, C$_1$–C$_{12}$alkyl, C$_5$–C$_7$cycloalkyl which is unsubstituted or substituted by 1, 2 or 3 C$_1$–C$_4$alkyl; C$_3$–C$_{12}$alkenyl, phenyl which is unsubstituted or substituted by 1, 2 or 3 C$_1$–C$_4$alkyl; benzyl which is unsubstituted or substituted on the phenyl by C$_1$–C$_4$alkyl; tetrahydrofurfuryl or C$_2$–C$_3$alkyl which is substituted in the 2 or 3 position by —OH, C$_1$–C$_4$alkoxy, di(C$_1$–C$_4$alkyl)amino or a group of the formula (III); or —N(R$_4$)(R$_5$) is additionally a group of the formula (III); and R$_6$ is hydrogen, C$_1$–C$_{12}$alkyl, C$_5$–C$_7$cycloalkyl which is unsubstituted or substituted by 1, 2 or 3 C$_1$–C$_4$alkyl; benzyl which is unsubstituted or substituted on the phenyl by 1, 2 or 3 C$_1$–C$_4$alkyl; tetrahydrofurfuryl, a group of the formula (IV) or C$_2$–C$_3$alkyl which is substituted in the 2 or 3 position by —OH, C$_1$–C$_4$alkoxy, di(C$_1$–C$_4$alkyl)amino or a group of the formula (III).

20. A mixture according to claim 16, wherein

R$_2$ is C$_2$–C$_8$alkylene;

A' is C$_1$–C$_8$acyl, (C$_1$–C$_8$alkoxy)carbonyl, cyclohexoxycarbonyl, C$_1$–C$_4$alkyl, cyclohexyl, allyl or benzyl;

A" is C$_1$–C$_4$alkyl, cyclohexyl or benzyl;

R$_3$, R$_4$ and R$_5$, which are identical or different, are hydrogen, C$_1$–C$_8$alkyl, cyclohexyl which is unsubstituted or substituted by methyl; C$_3$–C$_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —N($R_4$)($R_5$) is additionally 4-morpholinyl; and $R_6$ is hydrogen, $C_1$–$C_8$alkyl, cyclohexyl which is unsubstituted or substituted by methyl; benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

21. A mixture according to claim 16, wherein n is 2, 3, 4, 5, or 6;

the radicals $R_1$ are independently of one another hydrogen or methyl;

$R_2$ is $C_2$–$C_6$alkylene;

A' is $C_1$–$C_8$acyl, ($C_1$–$C_8$alkoxy)carbonyl, $C_1$–$C_4$alkyl or allyl;

A" is $C_1$–$C_4$alkyl;

the radicals B are independently of one another —N($R_4$)($R_5$) or a group of the formula (II);

$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl;

X is >$NR_6$; and $R_6$ is $C_1$–$C_4$alkyl.

22. A mixture according to claim 16, wherein

A' is acetyl, ($C_1$–$C_2$alkoxy)carbonyl or $C_1$–$C_4$alkyl; and

A" is $C_1$–$C_2$alkyl.

23. A mixture according to claim 16, wherein the molar ratio of the compound of the formula (C) to the compound of the formula (B) is 1:2 and n is 2, 4 and 6.

24. A composition containing an organic material susceptible to degradation induced by light, heat or oxidation and a mixture according to claim 16, with the proviso that the totality of the compounds of formula (I) present in the composition has a polydispersity $\overline{M}w/\overline{M}n$ of 1.1 to 1.5.

25. A composition according to claim 24, wherein the organic material is a synthetic polymer.

26. A composition according to claim 24, wherein the organic material is polyethylene or polypropylene.

27. A method for stabilizing an organic material against degradation induced by light, heat or oxidation, which comprises incorporating into said organic material a mixture according to claim 16, with the proviso that the totality of the compounds of formula (I) present in the organic material has a polydispersity $\overline{M}w/\overline{M}n$ of 1.1 to 1.5.

* * * * *